(12) United States Patent
Wiedenmann et al.

(10) Patent No.: US 9,034,599 B2
(45) Date of Patent: May 19, 2015

(54) POLYNUCLEOTIDES ENCODING MONOMERIC VARIANTS OF THE TETRAMERIC EQFP611

(71) Applicant: Universität Ulm, Ulm (DE)

(72) Inventors: Jörg Wiedenmann, Wasseralfingen (DE); Simone Kredel, Blaustein (DE); Franz Oswald, Ulm (DE); Gerd Ulrich Nienhaus, Blaustein (DE)

(73) Assignee: Universitat Ulm (DE)

( * ) Notice: Subject to any disclaimer, the term of this patent is extended or adjusted under 35 U.S.C. 154(b) by 0 days.

(21) Appl. No.: 14/164,903

(22) Filed: Jan. 27, 2014

(65) Prior Publication Data

US 2014/0255988 A1 Sep. 11, 2014

Related U.S. Application Data

(62) Division of application No. 13/131,291, filed as application No. PCT/EP2009/008413 on Nov. 26, 2009, now Pat. No. 8,680,238.

(60) Provisional application No. 61/118,130, filed on Nov. 26, 2008.

(51) Int. Cl.
| | |
|---|---|
| *C12P 21/06* | (2006.01) |
| *C12N 15/00* | (2006.01) |
| *C12N 5/00* | (2006.01) |
| *C12N 5/07* | (2010.01) |
| *C12N 1/20* | (2006.01) |
| *C12N 1/00* | (2006.01) |
| *C07K 14/435* | (2006.01) |
| *G01N 33/58* | (2006.01) |

(52) U.S. Cl.
CPC ..... *C07K 14/43504* (2013.01); *C07K 14/43595* (2013.01); *G01N 33/582* (2013.01)

(58) Field of Classification Search
None
See application file for complete search history.

(56) References Cited

FOREIGN PATENT DOCUMENTS

DE 197 18 640 7/1999

OTHER PUBLICATIONS

Kredel et al., Chemistry and Biology 15:224-233, 2008.*
Wiedenmann et al., J. Biomed. Optics 10:Jan./Feb. 2005, 7 pages.*
Shaner, N.C. et al., "Advances in Fluorescent Protein Technology," *Journal of Cell Science.*, 2007, vol. 120, pp. 4247-4260.
Matz, M.V. et al., "Fluorescent Proteins from Nonbioluminescent Anthozoa Species," *Nature Biotechnology*,Oct. 1999, vol. 17, pp. 969-973, 1227.
Yarbrough, J. et al., "Refined Crystal Structure of DsRed, a Red Fluorescent Protein from Coral, at 2.0-ÅResolution," *Proc. Natl. Acad. Sci. USA*, 2001, vol. 98, pp. 463-467.
Merzlyak, E.M. et al., "Bright Monomeric Red Fluorescent Protein with an Extended Fluorescence Lifetime," *Nature Methods*, Jul. 2007, vol. 4, No. 7, pp. 555-557.
Campbell, R.E. et al., A Monomeric Red Fluorescent Protein, *Proc. Natl. Acad. Sci. USA*, Jun. 2002, vol. 99, No. 12, pp. 7877-7882.
Karasawa, S., et al., Cyan-Emitting and Orange-Emitting Fluorescent Proteins as a Donor/Acceptor Pair for Fluorescence Resonance Energy Transfer, *Biochem. J.*, 2004, vol. 381, pp. 307-312.
Rizzo, M.A., et al., "An Improved Cyan Fluorescent Protein Variant Useful for FRET," *Nature Biotechnology*, Apr. 2004, vol. 22, No. 4, pp. 445-449.
Shcherbo, D. et al., "Bright Far-Red Fluorescent Protein for Whole-Body Imaging," *Nature Methods*, Sep. 2007, vol. 4, No. 9, pp. 741-746.
Schrader, M. et al., "The Peroxisome: Still a Mysterious Organelle," *Histochem. Cell Biol.*, 2008, vol. 129, pp. 421-440.
Schrader, M. et al., "Mitochondria and Peroxisomes: Are the 'Big Brother' and the 'Little Sister' Closer than Assumed?," *BioEssays*, 2007, vol. 29, pp. 1105-1114.
Beaucage, S.L. et al., "Deoxynucleoside Phosphoramidites—A New Class of Key Intermediates for Deoxypolynucleotide Synthesis," *Tetrahedron Letters*, 1981, vol. 22, No. 20, pp. 1859-1869.
Matthes, H.W.D. et al., "Simultaneous Rapid Chemical Synthesis of Over One Hundred Oligonucleotides on a Microscale," *EMBO Journal*, 1984, vol. 3, No. 4, pp. 801-805.
Saiki, R.K. et al., "Primer-Directed Enzymatic Amplification of DNA with a Thermostable DNA Polymerase," *Science*, Jan. 1988, vol. 239, pp. 487-491.
Kaufman, R.J. et al., "Amplification and Expression of Sequences Cotransfected with a Modular Dihydrofolate Reductase Complementary DNA Gene," *J. Mol. Biol.*, 1982, vol. 159, pp. 601-621.
Loyter, A. et al., "Mechanisms of DNA Uptake by Mammalian Cells: Fate of Exogenously Added DNA Monitored by the Use of Fluorescent Dyes," *Proc. Natl. Acad. Sci USA*, Jan. 1982, vol. 79, pp. 422-426.
Gleeson, M.A. et al., "Transformation of the Methylotrophic Yeast *Hansenula polymorpha*," *Journal of General Microbiology*, 1986, vol. 132, pp. 3459-3465.
Ho, S.N. et al., "Site-Directed Mutagenesis by Overlap Extension Using the Polymerase Chain Reaction,". *Gene*, 1989, vol. 77, pp. 51-59.
Munro S. et al., "A C-Terminal Signal Prevents Secretion of Luminal ER Proteins," *Cell*, Mar. 1987, vol. 48, pp. 899-907.
Shaner, et al., "Improved monomeric red, orange and yellow fluorescent proteins derived from *Discosoma* sp. Red fluorescent protein," *Nature Biotechnology*, vol. 22, No. 12, Dec. 2004, pp. 1567-1572.

* cited by examiner

*Primary Examiner* — David J Steadman
(74) *Attorney, Agent, or Firm* — DLA Piper LLP (US)

(57) ABSTRACT

DNA encoding a monomeric variant of red fluorescent protein eqFP611 comprising an amino acid sequence selected from the group consisting of SEQ ID No. 1, SEQ ID No. 3 and SEQ ID No. 5. DNA comprising a nucleotide sequence selected from the group consisting of SEQ ID No. 2, SEQ ID No. 4 and SEQ ID No. 6.

13 Claims, 6 Drawing Sheets

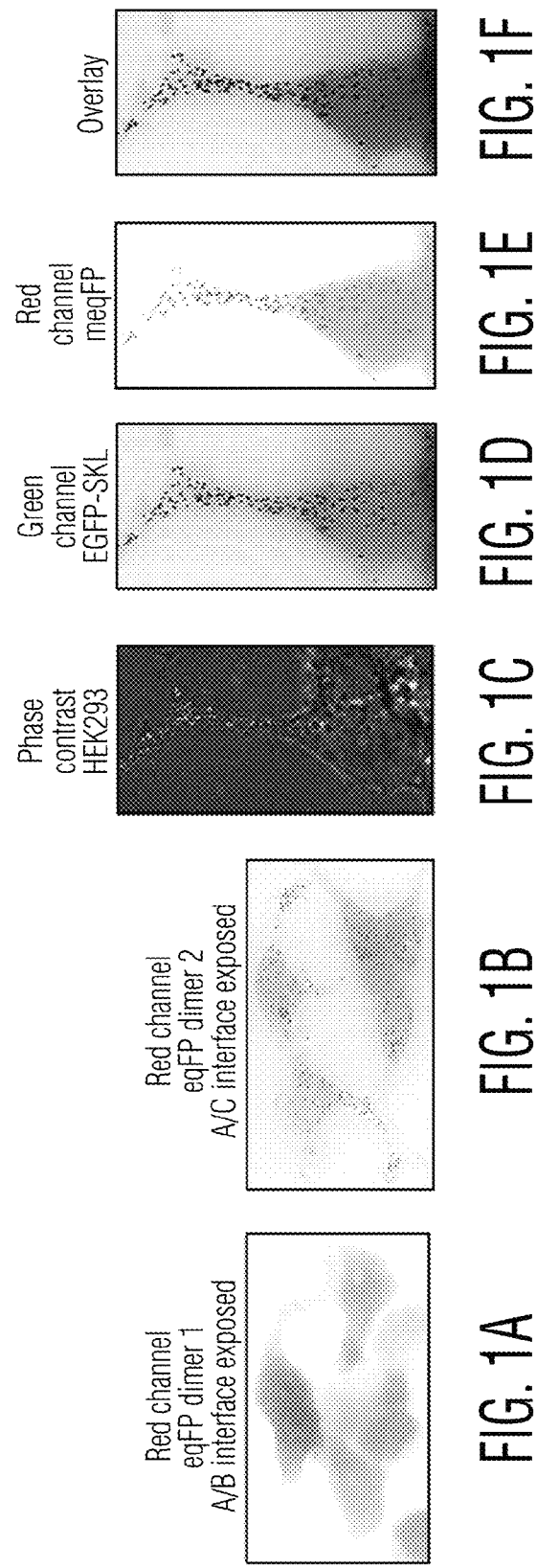

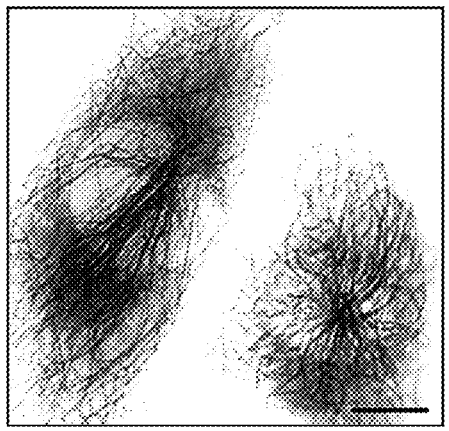 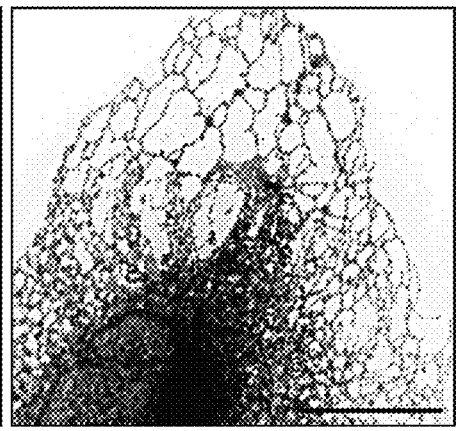
FIG. 3A    FIG. 3B
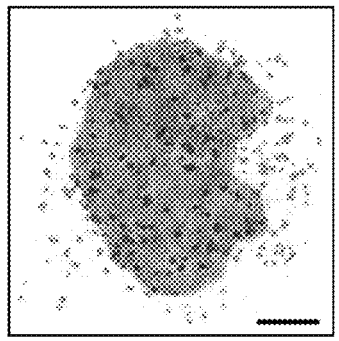 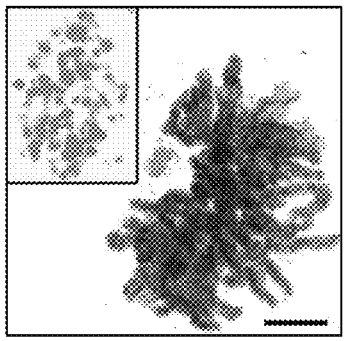 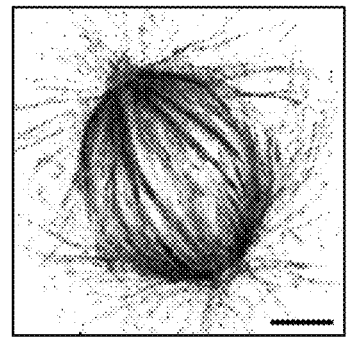
FIG. 4A    FIG. 4B    FIG. 4C

Fig.7

```
            ----------+---------+---------+---------+---------+---------+
eqFP611     MNS--------LIKENMRMMVVMEGSVNGYQFKCTGEGDGNPYMGTQTMRIKVVEGGPLP  52
mRuby       MNS--------LIKENMRMKVVLEGSVNGHQFKCTGEGEGNPYMGTQTMRIKVIEGGPLP  52
eqFP578     MSE--------LIKENMHMKLYMEGTVNNHHFKCTSEGERKPYEGTQTMKIKVVEGGPLP  52
TagRFP      MSE--------LIKENMHMKLYMEGTVNNHHFKCTSEGEGKPYEGTQTMRIKVVEGGPLP  52
mKate       MSE--------LIKENMHMKLYMEGTVNNHHFKCTSEGEGKPYEGTQTMRIKVVEGGPLP  52
DsRed       MRSSKN-----VIKEFMRFKVRMEGTVNGHEFEIEGEGEGRPYEGHNTVKLKVTKGGPLP  55
mRFP1       MASSED-----VIKEFMRFKVRMEGSVNGHEFEIEGEGEGRPYEGTQTAKLKVTKGGPLP  55
mCherry     MVSKGEEDNMAIIKEFMRFKVHMEGSVNGHEFEIEGEGEGRPYEGTQTAKLKVTKGGPLP  60
                                                         ⇒   ⇒    ⇒    ⇒

----------+---------+---------+---------+---------+---------+
eqFP611     FAFDILATSFMYGSKTFIKHTKGIPDFFKQSFPEGFTWERVTRYEDGGVFTVMQDTSLED 112
mRuby       FAFDILATSFMYGSKTFIKYPKGIPDFFKQSFPEGFTWERVTRYEDGGVITVMQDTSLED 112
eqFP578     FAFDILATSFMYGSKTFINHTQGIPDLFKQSFPEGFTWERITTYEDGGVLTATQDTSLQN 112
TagRFP      FAFDILATSFMYGSKTFINHTQGIPDFFKQSFPEGFTWERVTTYEDGGVLTATQDTSLQD 112
mKate       FAFDILATSFMYGSKTFINHTQGIPDFFKQSFPEGFTWERVTTYEDGGVLTATQDTSLQD 112
DsRed       FAWDILSPQFQYGSKVYVKHPADIPDYKKLSFPEGFKWERVMNFEDGGVVTVTQDSSLQD 115
mRFP1       FAWDILSPQFQYGSKAYVKHPADIPDYLKLSFPEGFKWERVMNFEDGGVVTVTQDSSLQD 115
mCherry     FAWDILSPQFMYGSKAYVKHPADIPDYLKLSFPEGFKWERVMNFEDGGVVTVTQDSSLQD 120
                                                          ⇒       ⇒

----------+---------+---------+---------+---------+---------+
eqFP611     GCLVYHAKVTGVNFPSNGAVMQKKTKGWEPNTEMLYPADGGLRGYSQMALNVDGGYLSC 172
mRuby       GCLVYHAQVRGVNFPSNGAVMQKKTKGWEPNTEMMYPADGGLRGYSHMALKVDGGHLSC 172
eqFP578     GCIIYNVKINGVNFPSNGSVMQKKTLGWEANTEMLYPADGGLRGHSQMALKLVGGGYLHC 172
TagRFP      GCLIYNVKIRGVNFPSNGPVMQKKTLGWEANTEMLYPADGGLEGRSDMALKLVGGGHLIC 172
mKate       GCLIYNVKIRGVNFPSNGPVMQKKTLGWEASTEMLYPADGGLEGRSDMALKLVGGGHLIC 172
DsRed       GCFIYKVKFIGVNFPSDGPVMQKKTMGWEASTERLYPRDGVLKGEIHKALKLKDGGHYLV 175
mRFP1       GEFIYKVKLRGTNFPSDGPVMQKKTMGWEASTERMYPEDGALKGEIKQRLKLKDGGHYDA 175
mCherry     GEFIYKVKLRGTNFPSDGPVMQKKTMGWEASSERMYPEDGALKGEIKQRLKLKDGGHYDA 180
              ⇒               ⇒          ⇒         ⇒    ⇒

----------+---------+---------+---------+---------+---------+
eqFP611     SFETTYRSKKTVENFKMPGFHFVDHRLERLEESDKEMFVVQHEHAVAKFCDLPSKLGRL  231
mRuby       SFVTTYRSKKTVGNIKMPGIHAVDHRLERLEESDNEMFVVQREHAVAKFAGLGGG      227
eqFP578     SFKTTYRSKKPAKNLKMPGFHFVDHRLERIKEADKETYVEQHEMAVAKYCDLPSKLGHR  231
TagRFP      NFKTTYRSKKPAKNLKMPGVYYVDHRLERIKEADKETYVEQHEVAVARYCDLPSKLGHK  231
mKate       WSKTTYRSKKPAKNLKMPGVYYVDHRLERIKEADKETYVEQHEVAVARYCDLPSKLGHK  231
DsRed       EFKSIYMAKKPVQ---LPGYYYVDSKLDITSHNEDYTIVEQYERTEGRHHLFL        225
mRFP1       EVKTTYMAKKPVQ---LPGAYKTDIKLDITSHNEDYTIVEQYERAEGRHSTGA        225
mCherry     EVKTTYKAKKPVQ---LPGAYNVNIKLDITSHNEDYTIVEQYERAEGRHSTGGMDELYK  236
              ⇒                  ⇒              ⇒
```

SEQUENCE LISTING

<160> NUMBER OF SEQ ID NOS: 29

<210> SEQ ID NO 1
<211> LENGTH: 227
<212> TYPE: PRT
<213> ORGANISM: Entacmaea quadricolor

<400> SEQUENCE: 1

Met Asn Ser Leu Ile Lys Glu Asn Met Arg Met Lys Val Val Leu Glu
1               5                   10                  15

Gly Ser Val Asn Gly His Gln Phe Lys Cys Thr Gly Glu Gly Glu Gly
            20                  25                  30

Asn Pro Tyr Met Gly Thr Gln Thr Met Arg Ile Lys Val Ile Glu Gly
        35                  40                  45

Gly Pro Leu Pro Phe Ala Phe Asp Ile Leu Ala Thr Ser Phe Met Tyr
    50                  55                  60

Gly Ser Arg Thr Phe Ile Lys Tyr Pro Lys Gly Ile Pro Asp Phe Phe
65                  70                  75                  80

Lys Gln Ser Phe Pro Glu Gly Phe Thr Trp Glu Arg Val Thr Arg Tyr
                85                  90                  95

Glu Asp Gly Gly Val Ile Thr Val Met Gln Asp Thr Ser Leu Glu Asp
            100                 105                 110

Gly Cys Leu Val Tyr His Ala Gln Val Arg Gly Val Asn Phe Pro Ser
        115                 120                 125

```
Asn Gly Ala Val Met Gln Lys Lys Thr Lys Gly Trp Glu Pro Asn Thr
            130                 135                 140
Glu Met Met Tyr Pro Ala Asp Gly Gly Leu Arg Gly Tyr Thr His Met
145                 150                 155                 160
Ala Leu Lys Val Asp Gly Gly His Leu Ser Cys Ser Phe Val Thr
                165                 170                 175
Thr Tyr Arg Ser Lys Lys Thr Val Gly Asn Ile Lys Met Pro Gly Ile
            180                 185                 190
His Ala Val Asp His Arg Leu Glu Arg Leu Glu Glu Ser Asp Asn Glu
        195                 200                 205
Met Phe Val Val Gln Arg Glu His Ala Val Ala Lys Phe Ala Gly Leu
    210                 215                 220
Gly Gly Gly
225

<210> SEQ ID NO 2
<211> LENGTH: 684
<212> TYPE: DNA
<213> ORGANISM: Entacmaea quadricolor

<400> SEQUENCE: 2
atgaattcac tgatcaagga aaatatgcgt atgaaggtgg tcctggaagg ttcggtcaac    60
ggccaccaat tcaaatgcac aggtgaagga aaggcaatc cgtacatggg aactcaaacc   120
atgaggatca aagtcatcga gggaggaccc ctgccatttg cctttgacat tcttgccacg   180
agcttcatgt atggcagccg tactttatc aagtacccga aaggcattcc tgatttcttt   240
aaacagtcct ttcctgaggg ttttacttgg aaagagtta caagatacga agatggtgga   300
gtcattaccg ttatgcagga caccagcctt gaggatggct gtctcgttta ccacgcccaa   360
gtcaggggg taaactttcc ctccaatggt gccgtgatgc agaagaagac caagggttgg   420
gagcctaata cagagatgat gtatccagca gatggtggtc tgaggggata cactcatatg   480
gcactgaaag ttgatggtgg tggccatctg tcttgctctt tcgtaacaac ttacaggtca   540
aaaaagaccg tcgggaacat caagatgccc ggtatccatg ccgttgatca ccgcctggaa   600
aggttagagg aaagtgacaa tgaaatgttc gtagtacaac gcgaacacgc agttgccaag   660
ttcgccgggc ttggtggtgg ttaa                                         684

<210> SEQ ID NO 3
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asn Ser Leu Ile Lys Glu Asn Met Arg Met Lys Val Val Leu Glu
1               5                   10                  15
Gly Ser Val Asn Gly His Gln Phe Lys Cys Thr Gly Glu Gly Glu Gly
            20                  25                  30
Asn Pro Tyr Met Gly Thr Gln Thr Met Arg Ile Lys Val Ile Glu Gly
        35                  40                  45
Gly Pro Leu Pro Phe Ala Phe Asp Ile Leu Ala Thr Ser Phe Met Tyr
    50                  55                  60
Gly Ser Arg Thr Phe Ile Lys Tyr Pro Lys Gly Ile Pro Asp Phe Phe
65                  70                  75                  80
```

```
Lys Gln Ser Phe Pro Glu Gly Phe Thr Trp Glu Arg Val Thr Arg Tyr
                85                  90                  95

Glu Asp Gly Gly Val Ile Thr Val Met Gln Asp Thr Ser Leu Glu Asp
            100                 105                 110

Gly Cys Leu Val Tyr His Ala Gln Val Arg Gly Val Asn Phe Pro Ser
        115                 120                 125

Asn Gly Ala Val Met Gln Lys Lys Thr Lys Gly Trp Glu Pro Asn Thr
    130                 135                 140

Glu Met Met Tyr Pro Ala Asp Gly Gly Leu Arg Gly Tyr Thr His Met
145                 150                 155                 160

Ala Leu Lys Val Asp Gly Gly His Leu Ser Cys Ser Phe Val Thr
                165                 170                 175

Thr Tyr Arg Ser Lys Lys Thr Val Gly Asn Ile Lys Met Pro Gly Ile
            180                 185                 190

His Ala Val Asp His Arg Leu Glu Arg Leu Glu Glu Ser Asp Asn Glu
        195                 200                 205

Met Phe Val Val Gln Arg Glu His Ala Val Ala Lys Phe Ala Gly Leu
    210                 215                 220

Gly Gly Gly
225

<210> SEQ ID NO 4
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgaacagcc tgatcaaaga aaacatgcgg atgaaggtgg tgctggaagg cagcgtgaac      60
ggccaccagt tcaagtgcac cggcgagggc gagggcaacc cctacatggg cacccagacc     120
atgcggatca agtgatcga gggcggacct ctgcccttcg ccttcgacat cctggccaca     180
tccttcatgt acggcagccg gaccttcatc aagtaccca agggcatccc cgatttcttc     240
aagcagagct ccccgaggg cttcacctgg gagagagtga ccagatacga ggacggcggc     300
gtgatcaccg tgatgcagga caccagcctg gaagatggct gcctggtgta ccatgcccag     360
gtcaggggcg tgaattttcc cagcaacggc gccgtgatgc agaagaaaac caagggctgg     420
gagcccaaca ccgagatgat gtaccccgct gacggcggac tgagaggcta cacccacatg     480
gccctgaagg tggacggcgg agggcacctg agctgcagct tcgtgaccac ctaccggtcc     540
aagaaaaccg tgggcaacat caagatgccc ggcatccacg ccgtggacca ccggctggaa     600
aggctggaag agtccgacaa cgagatgttc gtggtgcagc gggagcacgc cgtggccaag     660
ttcgccggcc tgggcggagg gtga                                            684

<210> SEQ ID NO 5
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asn Ser Leu Ile Lys Glu Asn Met Arg Met Lys Val Val Leu Glu
1               5                   10                  15
```

Gly Ser Val Asn Gly His Gln Phe Lys Cys Thr Gly Glu Gly Glu Gly
            20                  25                  30

Asn Pro Tyr Met Gly Thr Gln Thr Met Arg Ile Lys Val Ile Glu Gly
            35                  40                  45

Gly Pro Leu Pro Phe Ala Phe Asp Ile Leu Ala Thr Ser Phe Met Tyr
 50                  55                  60

Gly Ser Arg Thr Phe Ile Lys Tyr Pro Lys Gly Ile Pro Asp Phe Phe
 65                  70                  75                  80

Lys Gln Ser Phe Pro Glu Gly Phe Thr Trp Glu Arg Val Thr Arg Tyr
                85                  90                  95

Glu Asp Gly Gly Val Ile Thr Val Met Gln Asp Thr Ser Leu Glu Asp
            100                 105                 110

Gly Cys Leu Val Tyr His Ala Gln Val Arg Gly Val Asn Phe Pro Ser
            115                 120                 125

Asn Gly Ala Val Met Gln Lys Lys Thr Lys Gly Trp Glu Pro Asn Thr
130                 135                 140

Glu Met Met Tyr Pro Ala Asp Gly Gly Leu Arg Gly Tyr Thr His Met
145                 150                 155                 160

Ala Leu Lys Val Asp Gly Gly Gly His Leu Ser Cys Ser Phe Val Thr
                165                 170                 175

Thr Tyr Arg Ser Lys Lys Thr Val Gly Asn Ile Lys Met Pro Gly Ile
            180                 185                 190

His Ala Val Asp His Arg Leu Glu Arg Leu Glu Glu Ser Asp Asn Glu
            195                 200                 205

Met Phe Val Val Gln Arg Glu His Ala Val Ala Lys Phe Cys Asp Leu
            210                 215                 220

Pro Ser Lys Leu Gly Arg Leu
225                 230

<210> SEQ ID NO 6
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgaattcac tgatcaagga aaatatgcgt atgaaggtgg tcctggaagg ttcggtcaac    60
ggccaccaat tcaaatgcac aggtgaagga aaggcaatc cgtacatggg aactcaaacc   120
atgaggatca aagtcatcga gggaggaccc ctgccatttg cctttgacat tcttgccacg   180
agcttcatgt atggcagccg tacttttatc aagtacccga aaggcattcc tgatttcttt   240
aaacagtcct ttcctgaggg ttttacttgg gaaagagtta caagatacga agatggtgga   300
gtcattaccg ttatgcagga caccagcctt gaggatggct gtctcgttta ccacgcccaa   360
gtcagggggg taaactttcc ctccaatggt gccgtgatgc agaagaagac caagggttgg   420
gagcctaata cagagatgat gtatccagca gatggtggtc tgagggggata cactcatatg   480 gcactgaaag ttgatggtgg tggccatctg tcttgctctt cgtaacaac ttacaggtca   540 aaaaagaccg tcgggaacat caagatgccc ggtatccatg ccgttgatca ccgcctggaa   600
aggttagagg aaagtgacaa tgaaatgttc gtagtacaac gcgaacacgc agttgccaag   660
ttctgtgacc ttccatccaa actgggacgt cttttga                             696

```
<210> SEQ ID NO 7
<211> LENGTH: 4
<212> TYPE: PRT
<213> ORGANISM: Homo sapiens

<400> SEQUENCE: 7

Lys Asp Glu Leu
1

<210> SEQ ID NO 8
<211> LENGTH: 10
<212> TYPE: PRT
<213> ORGANISM: Entacmaea quadricolor

<400> SEQUENCE: 8

Cys Asp Leu Pro Ser Lys Leu Gly Arg Leu
1               5                   10

<210> SEQ ID NO 9
<211> LENGTH: 6
<212> TYPE: PRT
<213> ORGANISM: Entacmaea quadricolor

<400> SEQUENCE: 9

Ala Gly Leu Gly Gly Gly
1               5

<210> SEQ ID NO 10
<211> LENGTH: 21
<212> TYPE: PRT
<213> ORGANISM: Mus sp.

<400> SEQUENCE: 10

Met Glu Thr Asp Thr Leu Leu Leu Trp Val Leu Leu Leu Trp Val Pro
1               5                   10                  15

Gly Ser Thr Gly Asp
            20

<210> SEQ ID NO 11
<211> LENGTH: 16
<212> TYPE: PRT
<213> ORGANISM: Entacmaea quadricolor

<400> SEQUENCE: 11

His Ala Val Ala Lys Phe Cys Asp Leu Pro Ser Lys Leu Gly Arg Leu
1               5                   10                  15

<210> SEQ ID NO 12
<211> LENGTH: 10
<212> TYPE: PRT
<213> ORGANISM: Entacmaea quadricolor

<400> SEQUENCE: 12

His Ala Val Ala Lys His Ser Gly Leu Leu
1               5                   10

<210> SEQ ID NO 13
<211> LENGTH: 9
<212> TYPE: PRT
<213> ORGANISM: Entacmaea quadricolor

<400> SEQUENCE: 13

His Ala Val Ala Lys His Ser Gly Leu
1               5
```

<210> SEQ ID NO 14
<211> LENGTH: 9
<212> TYPE: PRT
<213> ORGANISM: Entacmaea quadricolor

<400> SEQUENCE: 14

His Ala Val Ala Lys Phe Ala Gly Leu
1               5

<210> SEQ ID NO 15
<211> LENGTH: 10
<212> TYPE: PRT
<213> ORGANISM: Entacmaea quadricolor

<400> SEQUENCE: 15

His Ala Glu Ala Gln Phe Ser Gly Leu Leu
1               5                   10

<210> SEQ ID NO 16
<211> LENGTH: 8
<212> TYPE: PRT
<213> ORGANISM: Entacmaea quadricolor

<400> SEQUENCE: 16

His Ala Val Ala Lys His Ser Gly
1               5

<210> SEQ ID NO 17
<211> LENGTH: 10
<212> TYPE: PRT
<213> ORGANISM: Entacmaea quadricolor

<400> SEQUENCE: 17

His Ala Val Ala Lys His Ser Gly Gly Gly
1               5                   10

<210> SEQ ID NO 18
<211> LENGTH: 8
<212> TYPE: PRT
<213> ORGANISM: Entacmaea quadricolor

<400> SEQUENCE: 18

His Ala Glu Ala Gln Phe Ser Gly
1               5

<210> SEQ ID NO 19
<211> LENGTH: 9
<212> TYPE: PRT
<213> ORGANISM: Entacmaea quadricolor

<400> SEQUENCE: 19

His Ala Val Ala Lys Phe Cys Asp Leu
1               5

<210> SEQ ID NO 20
<211> LENGTH: 10
<212> TYPE: PRT
<213> ORGANISM: Entacmaea quadricolor

<400> SEQUENCE: 20

His Ala Val Ala Lys Phe Ala Gly Gly Gly
1               5                   10

<210> SEQ ID NO 21

```
<211> LENGTH: 12
<212> TYPE: PRT
<213> ORGANISM: Entacmaea quadricolor

<400> SEQUENCE: 21

His Ala Val Ala Lys Phe Ala Gly Leu Gly Gly Gly
1               5                   10

<210> SEQ ID NO 22
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Met or Lys
<220> FEATURE:
<221> NAME/KEY: MOD_RES
<222> LOCATION: (15)..(15)
<223> OTHER INFORMATION: Met or Leu
<220> FEATURE:
<221> NAME/KEY: MOD_RES
<222> LOCATION: (22)..(22)
<223> OTHER INFORMATION: Tyr or His
<220> FEATURE:
<221> NAME/KEY: MOD_RES
<222> LOCATION: (31)..(31)
<223> OTHER INFORMATION: Asp or Glu
<220> FEATURE:
<221> NAME/KEY: MOD_RES
<222> LOCATION: (46)..(46)
<223> OTHER INFORMATION: Val or Ile
<220> FEATURE:
<221> NAME/KEY: MOD_RES
<222> LOCATION: (67)..(67)
<223> OTHER INFORMATION: Lys or Arg
<220> FEATURE:
<221> NAME/KEY: MOD_RES
<222> LOCATION: (72)..(72)
<223> OTHER INFORMATION: His or Tyr
<220> FEATURE:
<221> NAME/KEY: MOD_RES
<222> LOCATION: (73)..(73)
<223> OTHER INFORMATION: Thr or Pro
<220> FEATURE:
<221> NAME/KEY: MOD_RES
<222> LOCATION: (102)..(102)
<223> OTHER INFORMATION: Phe or Ile
<220> FEATURE:
<221> NAME/KEY: MOD_RES
<222> LOCATION: (120)..(120)
<223> OTHER INFORMATION: Lys or Gln
<220> FEATURE:
<221> NAME/KEY: MOD_RES
<222> LOCATION: (147)..(147)
<223> OTHER INFORMATION: Leu or Met
<220> FEATURE:
<221> NAME/KEY: MOD_RES
<222> LOCATION: (158)..(158)
<223> OTHER INFORMATION: Ser or Thr
<220> FEATURE:
<221> NAME/KEY: MOD_RES
<222> LOCATION: (159)..(159)
<223> OTHER INFORMATION: Gln or His
<220> FEATURE:
<221> NAME/KEY: MOD_RES
<222> LOCATION: (163)..(163)
<223> OTHER INFORMATION: Asn or Lys
<220> FEATURE:
<221> NAME/KEY: MOD_RES
<222> LOCATION: (169)..(169)
<223> OTHER INFORMATION: Tyr or His
<220> FEATURE:
<221> NAME/KEY: MOD_RES
```

```
<222> LOCATION: (175)..(175)
<223> OTHER INFORMATION: Glu or Val
<220> FEATURE:
<221> NAME/KEY: MOD_RES
<222> LOCATION: (185)..(185)
<223> OTHER INFORMATION: Glu or Gly
<220> FEATURE:
<221> NAME/KEY: MOD_RES
<222> LOCATION: (187)..(187)
<223> OTHER INFORMATION: Phe or Ile
<220> FEATURE:
<221> NAME/KEY: MOD_RES
<222> LOCATION: (192)..(192)
<223> OTHER INFORMATION: Phe or Ile
<220> FEATURE:
<221> NAME/KEY: MOD_RES
<222> LOCATION: (194)..(194)
<223> OTHER INFORMATION: Phe or Ala
<220> FEATURE:
<221> NAME/KEY: MOD_RES
<222> LOCATION: (207)..(207)
<223> OTHER INFORMATION: Lys or Asn
<220> FEATURE:
<221> NAME/KEY: MOD_RES
<222> LOCATION: (214)..(214)
<223> OTHER INFORMATION: His or Arg
<220> FEATURE:
<221> NAME/KEY: MOD_RES
<222> LOCATION: (222)..(222)
<223> OTHER INFORMATION: Cys or Ala
<220> FEATURE:
<221> NAME/KEY: MOD_RES
<222> LOCATION: (223)..(223)
<223> OTHER INFORMATION: Asp or Gly
<220> FEATURE:
<221> NAME/KEY: MOD_RES
<222> LOCATION: (225)..(225)
<223> OTHER INFORMATION: Pro or Gly
<220> FEATURE:
<221> NAME/KEY: MOD_RES
<222> LOCATION: (226)..(226)
<223> OTHER INFORMATION: Ser or Gly
<220> FEATURE:
<221> NAME/KEY: MOD_RES
<222> LOCATION: (227)..(227)
<223> OTHER INFORMATION: Lys or Gly

<400> SEQUENCE: 22

Met Asn Ser Leu Ile Lys Glu Asn Met Arg Met Xaa Val Val Xaa Glu
1               5                   10                  15

Gly Ser Val Asn Gly Xaa Gln Phe Lys Cys Thr Gly Glu Gly Xaa Gly
            20                  25                  30

Asn Pro Tyr Met Gly Thr Gln Thr Met Arg Ile Lys Val Xaa Glu Gly
        35                  40                  45

Gly Pro Leu Pro Phe Ala Phe Asp Ile Leu Ala Thr Ser Phe Met Tyr
50                  55                  60

Gly Ser Xaa Thr Phe Ile Lys Xaa Xaa Lys Gly Ile Pro Asp Phe Phe
65                  70                  75                  80

Lys Gln Ser Phe Pro Glu Gly Phe Thr Trp Glu Arg Val Thr Arg Tyr
                85                  90                  95

Glu Asp Gly Gly Val Xaa Thr Val Met Gln Asp Thr Ser Leu Glu Asp
            100                 105                 110

Gly Cys Leu Val Tyr His Ala Xaa Val Thr Gly Val Asn Phe Pro Ser
        115                 120                 125

Asn Gly Ala Val Met Gln Lys Lys Thr Lys Gly Trp Glu Pro Asn Thr
    130                 135                 140

Glu Met Xaa Tyr Pro Ala Asp Gly Gly Leu Arg Gly Tyr Xaa Xaa Met
145                 150                 155                 160
```

```
Ala Leu Xaa Val Asp Gly Gly Xaa Leu Ser Cys Ser Phe Xaa Thr
            165                 170                 175

Thr Tyr Arg Ser Lys Lys Thr Val Xaa Asn Xaa Lys Met Pro Gly Xaa
        180                 185                 190

His Xaa Val Asp His Arg Leu Glu Arg Leu Glu Glu Ser Asp Xaa Glu
        195                 200                 205

Met Phe Val Val Gln Xaa Glu His Ala Val Ala Lys Phe Xaa Xaa Leu
        210                 215                 220

Xaa Xaa Xaa Leu Gly Arg Leu
225             230

<210> SEQ ID NO 23
<211> LENGTH: 231
<212> TYPE: PRT
<213> ORGANISM: Entacmaea quadricolor

<400> SEQUENCE: 23

Met Asn Ser Leu Ile Lys Glu Asn Met Arg Met Val Val Met Glu
1               5                   10                  15

Gly Ser Val Asn Gly Tyr Gln Phe Lys Cys Thr Gly Glu Gly Asp Gly
            20                  25                  30

Asn Pro Tyr Met Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Lys Thr Phe Ile Lys His Thr Lys Gly Ile Pro Asp Phe Phe
65                  70                  75                  80

Lys Gln Ser Phe Pro Glu Gly Phe Thr Trp Glu Arg Val Thr Arg Tyr
                85                  90                  95

Glu Asp Gly Gly Val Phe Thr Val Met Gln Asp Thr Ser Leu Glu Asp
            100                 105                 110

Gly Cys Leu Val Tyr His Ala Lys Val Thr Gly Val Asn Phe Pro Ser
        115                 120                 125

Asn Gly Ala Val Met Gln Lys Lys Thr Lys Gly Trp Glu Pro Asn Thr
    130                 135                 140

Glu Met Leu Tyr Pro Ala Asp Gly Gly Leu Arg Gly Tyr Ser Gln Met
145                 150                 155                 160

Ala Leu Asn Val Asp Gly Gly Tyr Leu Ser Cys Ser Phe Glu Thr
            165                 170                 175

Thr Tyr Arg Ser Lys Lys Thr Val Glu Asn Phe Lys Met Pro Gly Phe
        180                 185                 190

His Phe Val Asp His Arg Leu Glu Arg Leu Glu Glu Ser Asp Lys Glu
        195                 200                 205

Met Phe Val Val Gln His Glu His Ala Val Ala Lys Phe Cys Asp Leu
        210                 215                 220

Pro Ser Lys Leu Gly Arg Leu
225             230

<210> SEQ ID NO 24
<211> LENGTH: 231
<212> TYPE: PRT
<213> ORGANISM: Entacmaea quadricolor

<400> SEQUENCE: 24

Met Ser Glu Leu Ile Lys Glu Asn Met His Met Lys Leu Tyr Met Glu
1               5                   10                  15
```

-continued

```
Gly Thr Val Asn Asn His His Phe Lys Cys Thr Ser Glu Gly Glu Arg
            20                  25                  30

Lys Pro Tyr Glu Gly Thr Gln Thr Met Lys Ile Lys Val Val Glu Gly
        35                  40                  45

Gly Pro Leu Pro Phe Ala Phe Asp Ile Leu Ala Thr Ser Phe Met Tyr
 50                  55                  60

Gly Ser Lys Thr Phe Ile Asn His Thr Gln Gly Ile Pro Asp Leu Phe
65                  70                  75                  80

Lys Gln Ser Phe Pro Glu Gly Phe Thr Trp Glu Arg Ile Thr Thr Tyr
                85                  90                  95

Glu Asp Gly Gly Val Leu Thr Ala Thr Gln Asp Thr Ser Leu Gln Asn
            100                 105                 110

Gly Cys Ile Ile Tyr Asn Val Lys Ile Asn Gly Val Asn Phe Pro Ser
        115                 120                 125

Asn Gly Ser Val Met Gln Lys Lys Thr Leu Gly Trp Glu Ala Asn Thr
130                 135                 140

Glu Met Leu Tyr Pro Ala Asp Gly Gly Leu Arg Gly His Ser Gln Met
145                 150                 155                 160

Ala Leu Lys Leu Val Gly Gly Gly Tyr Leu His Cys Ser Phe Lys Thr
                165                 170                 175

Thr Tyr Arg Ser Lys Lys Pro Ala Lys Asn Leu Lys Met Pro Gly Phe
            180                 185                 190

His Phe Val Asp His Arg Leu Glu Arg Ile Lys Glu Ala Asp Lys Glu
        195                 200                 205

Thr Tyr Val Glu Gln His Glu Met Ala Val Ala Lys Tyr Cys Asp Leu
    210                 215                 220

Pro Ser Lys Leu Gly His Arg
225                 230

<210> SEQ ID NO 25
<211> LENGTH: 231
<212> TYPE: PRT
<213> ORGANISM: Entacmaea quadricolor

<400> SEQUENCE: 25

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
 50                  55                  60

Gly Ser Arg Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Asn Thr
130                 135                 140

Glu Met Leu Tyr Pro Ala Asp Gly Gly Leu Glu Gly Arg Ser Asp Met
145                 150                 155                 160
```

```
Ala Leu Lys Leu Val Gly Gly His Leu Ile Cys Asn Phe Lys Thr
                165                 170                 175

Thr Tyr Arg Ser Lys Lys Pro Ala Lys Asn Leu Lys Met Pro Gly Val
                180                 185                 190

Tyr Tyr Val Asp His Arg Leu Glu Arg Ile Lys Glu Ala Asp Lys Glu
                195                 200                 205

Thr Tyr Val Glu Gln His Glu Val Ala Val Ala Arg Tyr Cys Asp Leu
                210                 215                 220

Pro Ser Lys Leu Gly His Lys
225                 230

<210> SEQ ID NO 26
<211> LENGTH: 231
<212> TYPE: PRT
<213> ORGANISM: Entacmaea quadricolor

<400> SEQUENCE: 26

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
                20                  25                  30

Lys Pro Tyr Glu Gly Thr Gln Thr Met Arg Ile Lys Val Val Glu Gly
                35                  40                  45

Gly Pro Leu Pro Phe Ala Phe Asp Ile Leu Ala Thr Ser Phe Met Tyr
            50                  55                  60

Gly Ser Lys Thr Phe Ile Asn His Thr Gln Gly Ile Pro Asp Phe Phe
65              70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
                100                 105                 110

Gly Cys Leu Ile Tyr Asn Val Lys Ile Arg Gly Val Asn Phe Pro Ser
            115                 120                 125

Asn Gly Pro Val Met Gln Lys Lys Thr Leu Gly Trp Glu Ala Ser Thr
130                 135                 140

Glu Met Leu Tyr Pro Ala Asp Gly Gly Leu Glu Gly Arg Ser Asp Met
145                 150                 155                 160

Ala Leu Lys Leu Val Gly Gly His Leu Ile Cys Asn Leu Lys Thr
                165                 170                 175

Thr Tyr Arg Ser Lys Lys Pro Ala Lys Asn Leu Lys Met Pro Gly Val
                180                 185                 190

Tyr Tyr Val Asp Arg Arg Leu Glu Arg Ile Lys Glu Ala Asp Lys Glu
                195                 200                 205

Thr Tyr Val Glu Gln His Glu Val Ala Val Ala Arg Tyr Cys Asp Leu
                210                 215                 220

Pro Ser Lys Leu Gly His Lys
225                 230

<210> SEQ ID NO 27
<211> LENGTH: 225
<212> TYPE: PRT
<213> ORGANISM: Entacmaea quadricolor

<400> SEQUENCE: 27
```

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
210                 215                 220

Leu
225

<210> SEQ ID NO 28
<211> LENGTH: 225
<212> TYPE: PRT
<213> ORGANISM: Entacmaea quadricolor

<400> SEQUENCE: 28

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
            115                 120                 125

Phe Pro Ser Asp Gly Pro Val Met Gln Lys Lys Thr Met Gly Trp Glu
130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 29
<211> LENGTH: 236
<212> TYPE: PRT
<213> ORGANISM: Entacmaea quadricolor

<400> SEQUENCE: 29

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

US 9,034,599 B2

POLYNUCLEOTIDES ENCODING MONOMERIC VARIANTS OF THE TETRAMERIC EQFP611

TECHNICAL FIELD

This disclosure relates to monomeric variants of the red fluorescent protein eqFP611 (Genbank accession number AY130757) exhibiting a comparatively large Stokes shift in the orange red region of the spectrum between 557 and 630 nm, and their versatile fields of application in biology, in particular live-cell imaging.

BACKGROUND

Fluorescent proteins (FPs) are powerful, specific marker tools for cellular imaging, and their range of applications is continuously expanding (1). Red fluorescent proteins (RFPs) are of particular interest as they extend the color palette for multi-channel and FRET (fluorescence resonance energy transfer) imaging, and the reduced scattering of long-wavelength light makes them attractive as markers for deep-tissue imaging. A performance gap has been noticed for natural RFPs after isolation from marine invertebrates (2-4), in comparison to variants of the classical green fluorescent protein (GFP) (1). In particular, their tendency to form dimers or tetramers can be detrimental for fusion marker applications (4-6). Therefore, an entire "fruit basket" of monomeric FPs in many different hues was engineered from the tetrameric RFP DsRed (1, 7-8). Together with monomeric variants of GFP, eqFP578 and several reef coral proteins, the emission colors of these FPs cover a wide range from blue to red (1, 6, 9-10). Bright far-red fluorescent markers with emission maxima shifted up to 639 nm were developed on the basis of the *Entacmaea quadricolor* proteins eqFP578 (11).

Important FP applications are in biosensors that report on intracellular conditions via fluorescence resonance energy transfer (FRET) between two or more chromophors (1, 9-10). A large Stokes shift, i.e., a large wavelength separation between excitation and emission peaks assists in channel separation and facilitates the use of FPs in FRET-based applications, in multi-color imaging application and in whole-body and deep tissue imaging. Several red fluorescent proteins with Stokes shifts>47 are characterized by excitation/emission peaks beyond 582/629 nm. In contrast, there is no fluorescent protein known which exhibits a comparably large Stokes shift in the orange red region of the spectrum between 557 and 630 nm.

Accordingly, it could be helpful to provide novel monomeric fluorescent proteins having a comparably large Stokes shift in the orange red region of the spectrum between 557 and 630 nm, in particular to facilitate biological imaging or imaging applications.

SUMMARY

We provide a monomeric variant of red fluorescent protein eqFP611 including an altered amino sequence having at least one amino acid exchange selected from the group consisting of M12K, M15L, Y22H, D31E, V46I, K67R, H72Y, T73P, F102I, K120Q, L147M, S158T, Q159H, N163K, Y169H, E185G, F187I, F192I, F194A, E175V, K207N, H214R, C222A, D223G, P225G, S226G and K227G.

We also provide a monomeric variant of red fluorescent protein eqFP611 including an amino acid sequence selected from the group consisting of SEQ ID No. 1, SEQ ID No. 3 and SEQ ID No. 5.

We further provide a fusion protein including a protein of interest fused to the monomeric variant of the red fluorescent protein eqFP611.

We still further provide a composition including the monomeric variant of the red fluorescent protein eqFP611 in a biologically compatible medium.

We further yet provide DNA encoding a monomeric variant of red fluorescent protein eqFP611 including an amino acid sequence selected from the group consisting of SEQ ID No. 1, SEQ ID No. 3 and SEQ ID No. 5.

We also further provide DNA including a nucleotide sequence selected from the group consisting of SEQ ID No. 2, SEQ ID No. 4 and SEQ ID No. 6.

We yet again provide an expression vector including expression control sequences operably linked to the DNA.

We further yet again provide a host cell including the DNA.

We also yet again provide a fluorescent reagent kit including at least one of a) DNA of SEQ ID No. 2, 4 or 6, b) an expression vector having DNA of SEQ ID No. 2, 4 or 6, and c) a host cell having DNA of SEQ ID No. 2, 4 or 6.

We still yet again provide a method of preparing a monomeric variant of red fluorescent protein eqFP611 including a) cultivating the host cell so that the host cell produces a monomeric variant of the red fluorescent protein eqFP611, and b) isolating and purifying the monomeric variant so produced by the host cell.

We also provide a method of selecting cells expressing a protein of interest including (a) introducing into cells DNA encoding a protein of interest and DNA encoding the monomeric variant of the red fluorescent protein eqFP611, (b) cultivating the cells from (a) under conditions permitting expression of the monomeric variant and the protein of interest, and (c) selecting cultivated cells from (b) which express the monomeric variant.

We also provide a method of measuring expression of a protein of interest in a cell including (a) introducing into a cell DNA encoding the monomeric variant of the red fluorescent protein eqFP611 fused to DNA encoding a protein of interest, the DNA being operably linked to and under control of an expression control sequence which moderates expression of the protein of interest, (b) cultivating the cell under conditions suitable for expression of the protein of interest, and (c) detecting fluorescence emission of the monomeric variant to measure expression of the protein of interest.

We also provide a method of determining localization of a protein of interest including (a) introducing into a cell DNA encoding the monomeric variant of the red fluorescent protein eqFP611 fused to a DNA encoding a protein of interest, the DNA being operably linked to and under control of a suitable expression control sequence, (b) cultivating the cell under conditions suitable for expression of the protein of interest; and (c) determining localization of the protein of interest by detecting fluorescence emission of the monomeric variant by optical means.

We also provide a method of localizing a subcellular structure in a cell including (a) introducing into a cell DNA encoding the monomeric variant of the red fluorescent protein eqFP611 fused to a DNA encoding a protein specific for a subcellular structure, the DNA being operably linked to and under control of an expression control sequence which moderates expression of the protein specific for a subcellular structure, (b) cultivating the cell under conditions suitable for expression of the protein specific for a subcellular structure; and (c) detecting fluorescence emission of the monomeric variant to localize the subcellular structure in the cell.

We also provide a method of comparing an effect of one or more test substance(s) on expression and/or localization of a protein of interest including (a) introducing into a cell DNA encoding the monomeric variant of the red fluorescent protein eqFP611 fused to a DNA encoding a protein of interest, the DNA being operably linked to and under control of a suitable expression control sequence, (b) cultivating the cell under conditions suitable for expression of the protein of interest in the presence and absence of the test substance(s), (c) determining expression and/or localization of the protein of interest by detecting fluorescence emission of the monomeric variant by optical means, and (d) comparing the fluorescence emission obtained in the presence and absence of the test substance(s) to determine the effect of the test substance(s) on the expression and/or localization of the protein of interest.

We also provide a method of determining promoter activity in a cell including (a) introducing into a cell a vector that is constructed such that DNA encoding the monomeric variant of the red fluorescent protein eqFP611 is located downstream of a promoter to be tested, and (b) detecting fluorescence of the monomeric variant to determine activity of the promoter.

BRIEF DESCRIPTION OF THE DRAWINGS

FIG. 1A shows subcellular localization in HEK293 cells with eqFP611 dimer 1 (RFP611, T122R) (13) evenly distributed over the cell.

FIG. 1B shows subcellular localization in HEK293 cells with the enhanced eqFP611 dimer 2 (T122G, F194A) in granular localization.

FIG. 1C is a phase contrast image of cells co-expressing EGFP-SKL and an enhanced monomeric eqFP611 (T122R, F194A) variant.

FIG. 1D is a green-channel image of cells co-expressing EGFP-SKL and an enhanced monomeric eqFP611 (T122R, F194A) variant.

FIG. 1E is red-channel image produced with a standard TRITC filter set of cells co-expressing EGFP-SKL and an enhanced monomeric eqFP611 (T122R, F194A) variant.

FIG. 1F is an overlay image of the green and red channels of cells co-expressing EGFP-SKL and an enhanced monomeric eqFP611 (T122R, F194A) variant.

FIG. 3A shows an epifluorescence image of NIH3T3 cells expressing the monomeric eqFP611 variant fused to human α-tubulin. Two cells from a single image were arranged in closer proximity.

FIG. 3B shows a spinning-disk confocal image of the endoplasmic reticulum of a HeLa cell stained with ER-monomeric-eqFP611-variant-KDEL ("KDEL" disclosed as SEQ ID No. 7). False colors encode fluorescence intensity.

FIG. 4A is a confocal image (Leica TCS 4Pi) of HEK293 cells co-expressing monomeric eqFP611 variant-PTS and H$_2$B-EGFP during interphase. Bars: 2 µm.

FIG. 4B is a confocal image (Leica TCS 4Pi) of HEK293 cells co-expressing monomeric eqFP611 variant-PTS and H$_2$B-EGFP during metaphase. The inset in shows a magnification of a peroxisomal cluster. Bars: 2 µm.

FIG. 4C is a confocal image (Leica TCS 4Pi) of HEK293 cells co-expressing monomeric eqFP611 variant-PTS and H$_2$B-EGFP with tubulin fibers labeled in green with Alexa Fluor®-488 via an anti-α-tubulin antibody to reveal peroxisomal clustering at the spindle poles. Bars: 2 µm.

FIG. 7 displays a multiple sequence alignment of monomeric red fluorescent proteins and their tetrameric predecessors (SEQ ID Nos. 23, 1 and 24-29, respectively, in order of appearance). Modified amino acid residues are highlighted in different colors; cyan: residues involved in interface interactions; green: residues in the interior of the .beta.-can; magneta: residues interacting with the chromophore; yellow: external residues; gray: GFP-termini of mCherry. The chromophore is underlined; .beta.-strands are indicated by arrows.

DETAILED DESCRIPTION

Figures 2A, 2B, 2C, 2D:
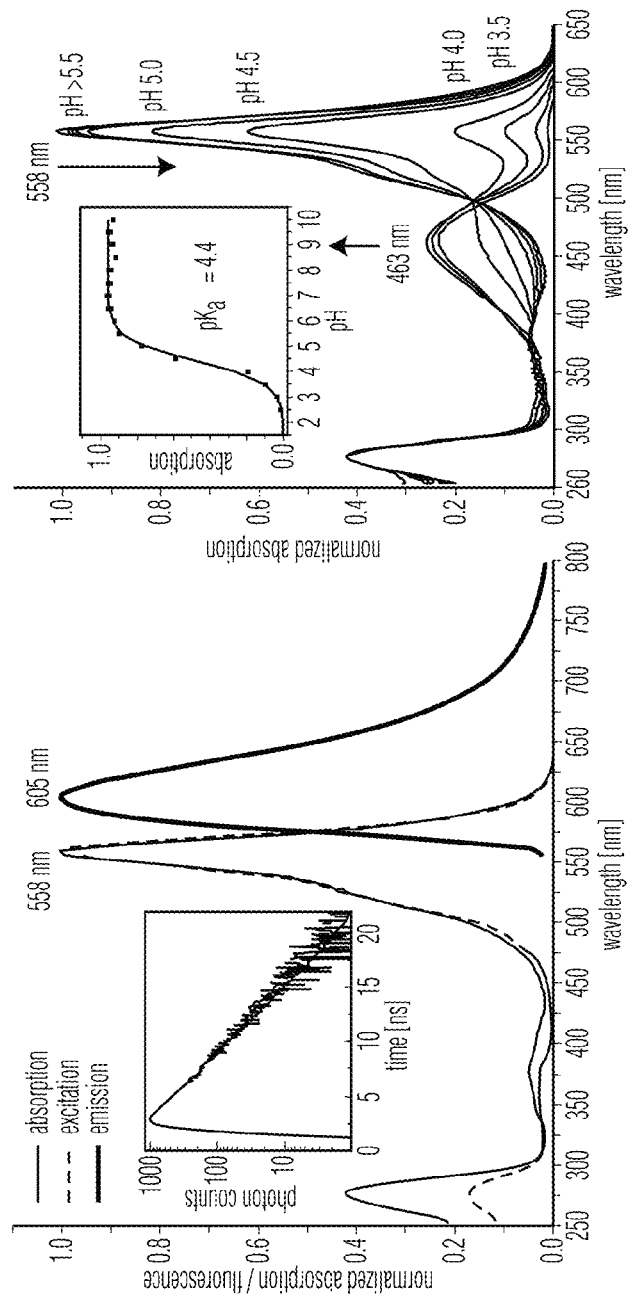
FIG. 2A shows in vitro chromophore maturation at 37° C. as determined from the fluorescence emission at 605 nm (solid line: exponential fit).
FIG. 2B shows elution volume for concentrations of 4-30 mg/ml (0.16-1.2 mM) during gel-filtration analysis (standards for the oligomerization degree: GFP S65T, monomer; td-RFP611, dimer; eqFP611, tetramer).
FIG. 2C shows absorption, excitation and emission spectra (inset: fluorescence decay with exponential fit yielding a lifetime of 2.6.+−.0.1 ns).
FIG. 2D shows absorption spectra at various pH values (inset: absorption at 558 nm versus pH; Henderson-Hasselbalch fit reveals a pKa of 4.4).

We provide a monomeric variant of the red fluorescent protein eqFP611 having an altered amino sequence featuring at least one of the amino acid exchanges selected from the group consisting of M12K, M15L, Y22H, D31E, V46I, K67R, H72Y, T73P, F102I, K120Q, L147M, S158T, Q159H, N163K, Y169H, E185G, F187I, F192I, F194A, E175V, K207N, H214R, C222A, D223G, P225G, S226G and K227G.

The numbering of the above listed amino acid exchanges are based on the amino acid sequence of eqFP611 deposited under genbank accession number AY130757. Further, amino acids are described using the single letter code. In this regard, for instance the term "M12K" means that the amino acid M (methionine) at position 12 from the eqFP611 has been exchanged by the amino acid K (lysine).

More specifically, we provide a monomeric variant of the red fluorescent protein eqFP611 having an amino acid sequence selected from the group consisting of SEQ ID No. 1, SEQ ID No. 3 and SEQ ID No. 5. In this regard, the monomeric rqFP611 variant as set forth in SEQ ID No. 3 is a codon optimized variant of the monomeric eqFP611 variant as set forth in SEQ ID No. 1. The monomeric eqFP611 variant as set forth in SEQ ID No. 5 carries the C-terminal tail of eqFP611 as a natural peroxisomal targeting signal.

The monomeric red fluorescent proteins are created from the tetrameric red fluorescent protein eqFP611 from the sea anemone *Entacmaea quadricolor* (Genbank accession number AY130757). The monomeric eqFP611 variants are in particular useful as labeling substances, preferably for live-cell imaging as well for imaging of fixed cells. The fluorescent proteins are characterized by advantageous properties such as red fluorescence with a large Stokes shift, monomeric nature, functional expression at 37° C., functional localization in the endoplasmic reticulum of mammalian cells, functional expression in fusion with tubulin in NIH3T3 cells, superior stability of fluorescence in cells fixed with paraformaldehyde and superior stability at extreme pH values. Moreover, a variant is presented that allows labeling of peroxisomes in eukaryotic cells.

The F102I variant of the tetrameric eqFP611 was chosen as the starting material for the development of a monomeric variant owing to its excellent expression at 37°. Introduction of amino acids $_{122}$arginine and $_{194}$alanine, which were known to disrupt the A/B and A/C subunit interactions in tetrameric DsRed and eqFP611 (7, 12), resulted in a nearly complete loss of fluorescence. In several rounds of random and multi-site-directed mutagenesis, the fluorescence was recovered by replacing amino acids that apparently impeded proper folding and maturation of the chromophor. In HEK293 cells transfected with these monomeric eqFP611 variants, the red fluorescence was not evenly distributed but rather appeared as dot-like structures in the cytoplasm. This localization resembled closely the aggregates reported for several non-soluble GFP-like proteins such as dsRed. In-depth analysis of the sequence and observation of the behavior of the "aggregates" during the cell cycle revealed that exposure of the A/C interface during monomerization exposed a subcellular targeting signal that directs the protein in cellular organelles, namely the amino acid sequence $_{229}$GRL$_{231}$ at the C terminus of the monomeric eqFP611 variant as set forth in SEQ ID No. 5, and also the preceding triplet $_{226}$SKL$_{228}$ serve as (type-1) peroxisomal targeting signal (PTS) (13). The presence of a functional PTS was verified by imaging HEK293 cells co-transfected with monomeric eqFP611 as set forth in SEQ ID No. 5 and EGFP-SKL, an established peroxisomal marker. Both green and red fluorescence showed perfect co-localization (FIG. 1). We succeeded in removing peroxisomal targeting by replacing the C-terminal sequence $_{222}$CDLPSKLGRL$_{231}$ (SEQ ID No. 8) of eqFP611 by $_{222}$AGLGGG$_{227}$ (SEQ ID No. 9); amino acid modification and even truncation of the $_{229}$GRL$_{231}$ tripeptide did not suffice (Supplemental Table 1). After completion of seven rounds of random mutagenesis and four rounds of multi site-directed mutagenesis, a bright red-fluorescent monomer as set forth in SEQ ID No. 1 was finally obtained. Compared to wild-type eqFP611, it contains altogether 28 amino acid replacements and is shorter by four amino acids. Additional mutations may be introduced. For instance at least one amino acid exchange selected from the group consisting of N2Y/K/D, S3P, L4M, K6Q/E, NS8K, M11T, M12K/V/R/L, M15V/L, E16D, Y22H, T27I, E29K, D31E, N33S/K, Y35F, M36L/V/K, K44N/R/Q, V46I/A, I57V, K67R, H72Y, T73S/P, I76V/F, S83T, D98E, F102I/L/V, V104A, M105I, E111V, D112G, C114S, Y117H, A119V, K120R/Q, T122R/A/G/M, S128A/P, N129H/D, Q134R, K136R, M146I, L147M, Y148C, D151N, Y157H/F, S158T, Q159H, A161V, N163K/R, D165E, Y169H, S171F/Y, S173F, E175V; T183S/A, V184D/I, E185G, N186Y, F187I/L, K188Q/E, G191D, F192I/Y, F194A/V/T, H197Y, E204D, S205R, D206G, K207D/N/Q/E, M209K/T, Q213L, H214R, H216R/Y, V218E, F221I/S/L/Y, C222W/Y/G/C, L224P, P225S and L231P may be introduced in a monomeric variant of the red fluorescent protein eqFP611. These amino acid sequences may further improve folding of monomeric eqFP611 variants. To further improve the performance of the monomeric eqFP611 variant as set forth in SEQ ID No. 1 in live-cell imaging applications, the codon usage of the final variant was altered to facilitate expression. By this method, the fluorescence in mammalian cells could be increased by 5-8 fold. The codon optimized variant as set forth in SEQ ID No. 3 is particularly useful for labeling purposes in sensitive systems such as primary cell cultures or stem cells.

Figure 2E:
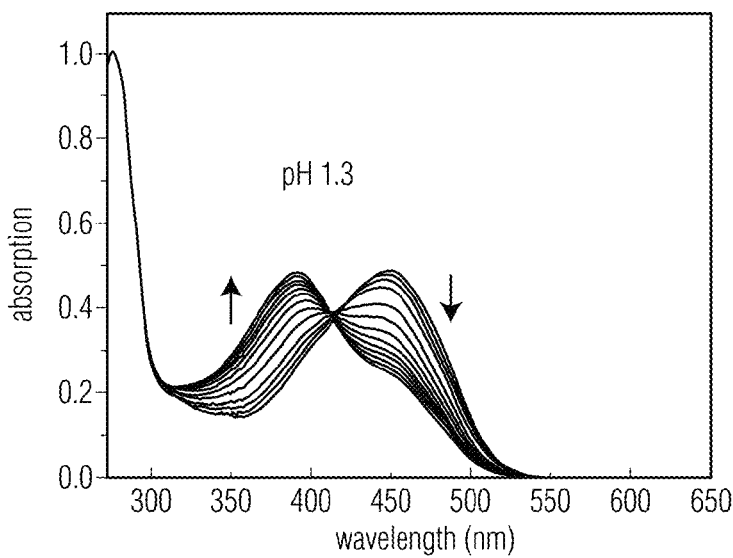
FIG. 2E shows the increasing absorption at about 390 nm along with the decrease of the about 463 nm band of the protonated chromophore of the monomeric eqFP611 variant indicates the destruction of the acylimine bond of the chromophore over a period of 3.5 h time at pH 1.3.
Figure 2F:
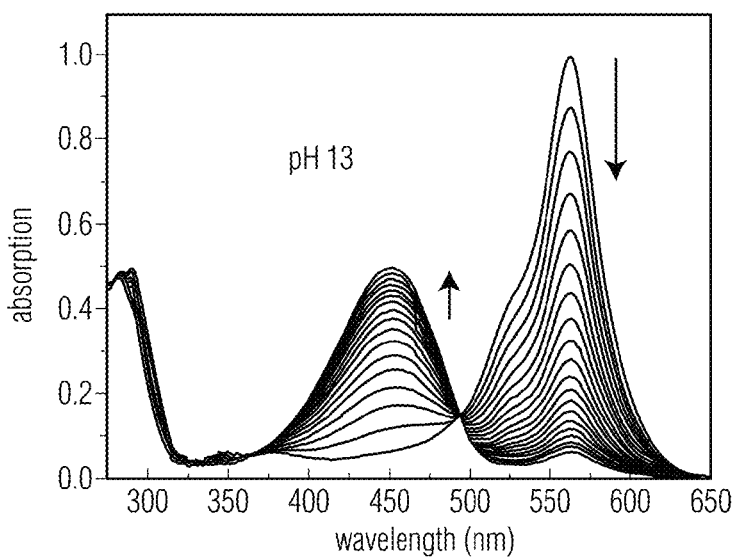
FIG. 2F shows changes in the absorption spectrum of the monomeric eqFP611 variant during a 1-h time course of alkaline denaturation at pH 13.
Figure 2G:
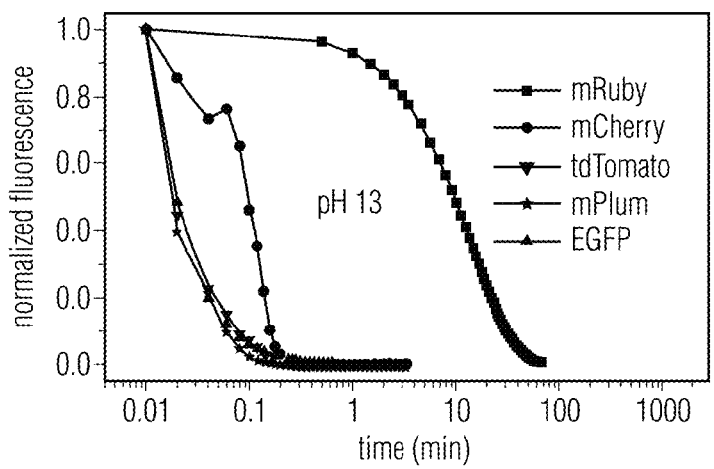
FIG. 2G shows time-dependent fluorescence decay of the monomeric eqFP611 variant at pH 13 in comparison to other monomeric fluorescent proteins, measured, at their emission maxima.

The following properties relate to the monomeric eqFP611 variant as set forth in SEQ ID No. 1 and 3. At 37° C., fluorescence spectrometry on dilute solutions of the purified protein yields a half-maturation time of 2.8 h, which makes the protein suitable for most cell biological imaging applications (FIG. 2A). A tendency to dimerize was absent in the entire range of physiologically relevant concentrations (FIG. 2B). With excitation and emission maxima at 558 nm and 605 nm, respectively, the eqFP611 variant combines a monomeric nature with a uniquely large Stokes shift in the orange-red emission region (FIG. 2C, Supplementary Table 2). Its fluorescence lifetime of 2.6±0.1 ns is comparatively long for a monomeric red fluorescent protein (6), and together with its high quantum yield (0.35) and molar extinction coefficient of 112,000 $M^{-1}$ $cm^{-1}$, the monomeric eqFP611 variant appears as superb marker in the red spectral range. It may be especially useful for FRET applications, where it bridges the gap between yellow-orange and far-red fluorescent proteins. The photobleaching probability of the monomeric eqFP611 variant ($5.3 \times 10^{-6}$) is very similar to the one of its predecessor RFP611 ($4.9 \times 10^{-6}$). The engineering process has significantly improved the stability of the monomeric eqFP611 variant at pH extremes as compared to tetrameric eqFP611. Below pH 5, the monomeric eqFP611 variant chromophore becomes protonated, as indicated by the increasing absorption band at 463 nm (FIG. 2D), but the protein remains stable even at pH 3. In contrast, the eqFP611 chromophore decomposes quickly at pH 3, as witnessed by the appearance of a 390-nm absorption band indicative of the neutral GFP (Green Fluorescent Protein) chromophore. At pH 13, the fluorescence of a variety of monomeric fluorescent proteins including EGFP (Enhanced Green Fluorescent Protein) disappears within seconds, whereas the fluorescence of the monomeric eqFP611 variant takes about an hour to vanish completely (FIGS. 2E-G). This stability at pH extremes makes the monomeric eqFP611 variant suitable for imaging of cellular organelles with pH values deviating from the standard physiological pH around pH 7. The stability of the monomeric eqFP611 variant is further beneficial for imaging of cells fixed with paraformaldehyde: The fluorescence of cells fixed in paraformaldehyde after expressing the state-of-the-art red fluorescent marker protein "mCherry" steadily faded in course of three weeks. In contrast, the fluorescence of cells expressing the monomeric eqFP611 variant slightly increased under the same experimental conditions. This property makes the monomeric eqFP611 variant an ideal marker for applications that rely on tracking of labeled cells or proteins in tissue fixed with paraformaldehyde.

Figures 6A, 6B:
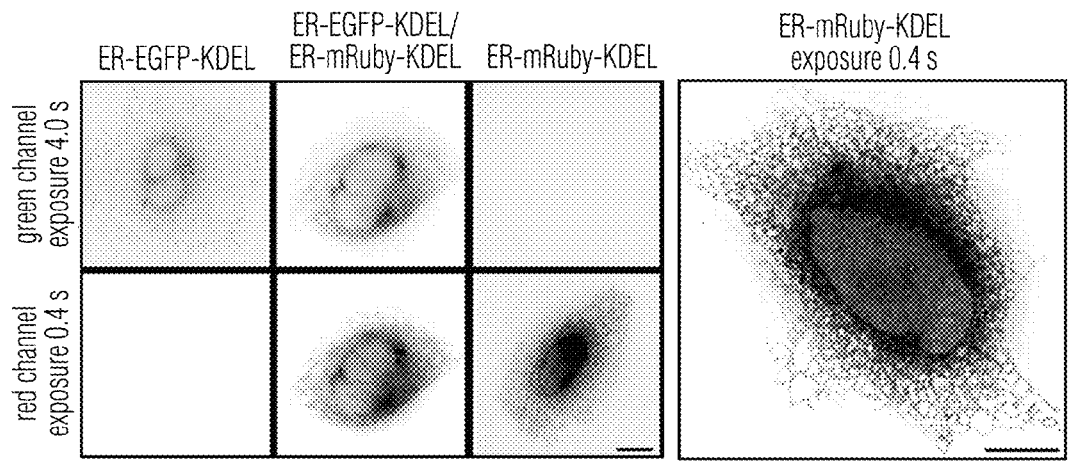
FIG. 6A shows a comparison of ER-staining in HeLa cells expressing ER-EGFP-KDEL ("KDEL" disclosed as SEQ ID No. 7) (left column), ER-monomeric eqFP611 variant-KDEL ("KDEL" disclosed as SEQ ID No. 7) (right column) or both (middle column). Imaging of the EGFP fluorescence in the green channel (upper row) required exposure times of 4.0 s whereas fluorescence of the monomeric eqFP611 variant in the red channel could be already recorded with exposure times of 0.4 s using an Olympus IX71 microscope equipped with standard FITC (green channel) and TRITC (red channel) filter sets. Bars: 2 µm.
FIG. 6B shows a magnified view of a HeLa cell expressing ER-monomeric eqFP611 variant-Kdel ("Kdel" disclosed as SEQ ID No. 7) photographed on the Olympus IX71 microscope with TRITC filter. Bars: 2 µm.

To examine the performance of the monomeric eqFP611 variant (as set forth in SEQ ID No. 1 or 3) as a marker in live-cell imaging applications, it was fused to the N-terminus of α-tubulin because imaging of microtubules with such a fusion construct is known to be very sensitive to oligomerization, aggregation tendency and C-terminal amino acid linker properties of the marker protein (8). FIG. 3A exemplifies an excellent performance of the monomeric variant in highlighting tubulin fibers. Another challenging application, which requires a high stability of the marker protein, is its localization in the endoplasmic reticulum (ER). The construct ER-monomeric eqFP611 variant-KDEL yielded excellent images of the ER with only 0.4 s light exposure in both epifluorescence and confocal microscopy modes (FIG. 3B, FIGS. 6A-B), whereas the popular marker protein EGFP targeted to the ER (ER-EGFP-KDEL) required much longer exposure times under comparable conditions (FIGS. 6A-B).

Figure 5:
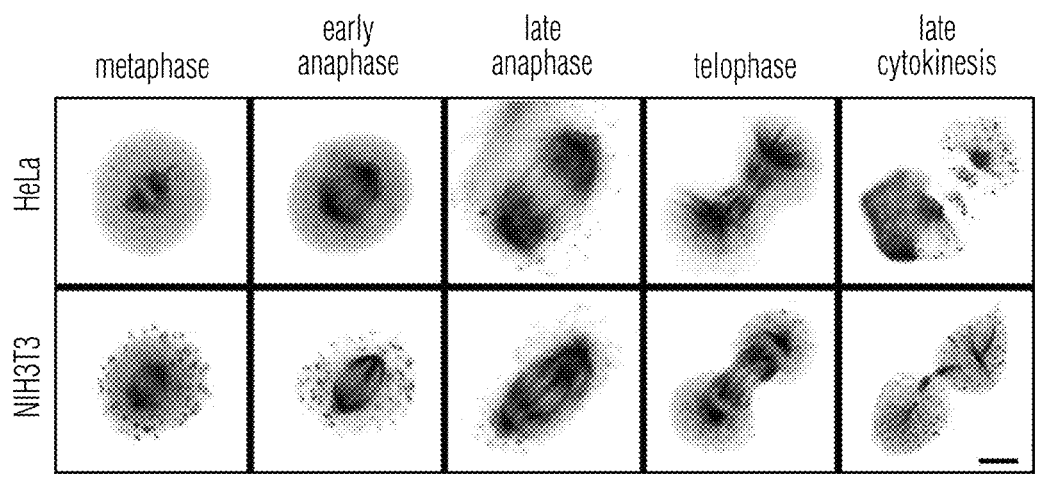
FIG. 5 shows the following: Inheritance of peroxisomes. Distribution of peroxisomes during different stages of mitosis in HeLa (upper row) and NIH3T3 cells (lower row). Peroxisomes are highlighted by monomeric eqFP611 variant-PTS. The spindle of the mitotic cells is stained with EGFP fused to a tubulin-binding protein [13]. Images were taken 24-48 h after transfection on an Olympus IX71 microscope equipped with standard FITC and TRITC filter sets. Bars: 5 µ·m.

Peroxisomes are the organelles that have been discovered last, and despite their essential functional roles in eukaryotic cells (13), many aspects of their biology are still not well understood (13). The present observation with the early monomeric eqFP611 variant as set forth in SEQ ID No. 5 that highlighted two peroxisome clusters during mitosis of HEK293 cells suggests an ordered partitioning of this organell to daughter cells. This finding contrasts the commonly held view that peroxisomes are distributed stochastically between dividing mammalian cells (14). Hence, it was further explored the issue of peroxisome inheritance in mammalian cells. To this end, the original C-terminal sequence of eqFP611 in the monomeric eqFP611 variant as set forth in SEQ ID No. 5 was restored to attain an efficient peroxisomal marker (monomeric eqFP611-PTS). HEK293 cells were co-transfected with monomeric eqFP611-PTS and the chromatin-binding histone 2B protein (H2B) fused to EGFP (1) so as to simultaneously image peroxisomes (in red) and chromatin (in green). During interphase, peroxisomes were seen to be evenly distributed over the cytoplasm (FIG. 2C). However, at the beginning of metaphase, peroxisomes began to congregate in two clusters on the bottom and top of the emerging metaphase plate (FIG. 2D). Additional immunochemical staining of the mitotic spindle revealed that the peroxisomes clustered around the spindle poles (FIG. 2E). By this ordered partitioning strategy, the cells can ensure that equal numbers of peroxisomes are inherited by the daughter cells. It was further examined this mechanism with two other mammalian cell lines. HeLa and NIH3T3. In HeLa cells, peroxisomes were also closely associated with the spindle pole during all stages of cell division (FIG. 5). By contrast, NIH3T3 cells showed these peroxisomal associations to the centrosomes only during two stages of cell division, anaphase and telophase.

We also provided a monomeric variant of the red fluorescent protein having an amino acid sequence comprising a deletion, substitution and/or addition of one or several amino acids with respect to the amino acid sequence selected from the group consisting of SEQ ID No. 1, 3 and 5 and having red fluorescent properties.

The range of "1 to several" in "an amino acid sequence comprising a deletion, substitution, and/or addition of one or several amino acids" is not particularly limited but means, for example, about 1 to 20, preferably 1 to 10, more preferably 1 to 7, furthermore preferably 1 to 5, and particularly preferably 1 to 3.

We also provide a fusion compound, preferably a fusion protein, comprising a protein of interest fused to a monomeric variant of the red fluorescent protein eqFP611. The type of protein of interest with which the monomeric eqFP611 variant is fused is not particularly limited. Preferred examples may include proteins localizing in cells, proteins specific for intracellular structures, in particular intracellular organelles and targeting signals (e.g., a nuclear transport signal, a mitochondrial presequence and the like). The obtained fusion protein wherein the monomeric eqFP611 variant is fused with a protein of interest is allowed to be expressed in cells. By monitoring a fluorescence emitted it becomes possible to analyze the activity, localization, processing, or dynamics of the protein of interest in cells. That is, cells transformed or transfected with DNA encoding the monomeric eqFP611 variant are observed with the fluorescence microscope, so that the activity, localization, processing and dynamics of the protein of interest in the cells can visualized and thus analyzed.

The term "protein of interest" is intended also to encompass polypeptides and peptide fragments. Examples of such proteins of interest include: NFκB and subunits thereof, RAC1, PLC domains, MAPKAP2, PKC, Cytochrome C, RHO, β-actin, α-tubulin, STAT6 and protein kinase C isotypes.

We further provide a composition comprising a monomeric eqFP611 variant and a suitable biologically compatible medium. Examples of suitable biologically compatible media include: Nutritive media, buffer solutions, pharmaceutically acceptable carriers.

We still further provide DNA encoding a monomeric variant of the red fluorescent protein eqFP611 having an amino acid sequence selected from the group consisting of SEQ ID No. 1, SEQ ID No. 3 and SEQ ID No. 5.

The DNA may have a nucleotide sequence selected from the group consisting of SEQ ID No. 2, SEQ ID No. 4 and SEQ ID No. 6.

Furthermore, we address a nucleotide sequence comprising a deletion, substitution and/or addition of one or several nucleotides with respect to the nucleotide sequence as set forth in SEQ ID No. 2, 4 or 6. The range of "1 to several" in "a nucleotide sequence comprising a deletion, substitution and/or addition of one or several nucleotides" is not particularly limited but means, for example, about 1 to 50, preferably 1 to 30, more preferably 1 to 20, furthermore preferably 1 to 10, and particularly preferably 1 to 5.

The DNA may be prepared synthetically by establishes methods, e.g., the phosphoramidite method (15, 16). According to the phosphoramidite method, oligonucleotides are synthesized, e.g., in an automatic DNA synthesizer, purified, annealed, ligated and cloned into suitable vectors. The DNA may also be prepared by recombinant DNA methodology (17). The DNA may also be prepared by polymerase chain reaction (PCR) (18).

The method of introducing a desired mutation into a predetermined nucleotide sequence is known. For example, DNA having the mutation can be constructed by appropriately using known techniques such as site specific mutagenesis method, PCR using degenerate oligonucleotides, and exposure of cells containing the nucleic acid to a mutagen or radiation (19, 20).

The DNA sequence encoding a monomeric eqFP611 variant may be joined in-frame with a gene encoding a protein of interest and the desired fusion protein produced when inserted into an appropriate expression vector. For example, polymerase chain reaction or complementary oligonucleotides may be employed to engineer a polynucleotide sequence corresponding to a monomeric eqFP611 variant, 5' or 3' to the gene sequence corresponding to the protein of interest. Alternatively, the same techniques may be used to engineer a polynucleotide sequence corresponding to the sequence of a monomeric eqFP611 variant 5' or 3' to the multiple cloning site of an expression vector prior to insertion of a gene sequence encoding the protein of interest. The polynucleotide sequence corresponding to the sequence of a monomeric eqFP611 may comprise additional nucleotide sequences to include cloning sites, linkers, transcription and translation initiation and/or termination signals, labeling and purification tags.

In a further aspect, there is provided an expression vector comprising suitable expression control sequences operably linked to a DNA molecule. The DNA may be inserted into a recombinant vector, which may be any vector that may be conveniently be subjected to recombinant DNA procedures. The choice of vector will often depend on the host cell into which it is to be introduced. Thus, the vector may be an autonomously replicating vector, e.g., a vector which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

The vector is preferably an expression vector in which the DNA sequence encoding a monomeric eqFP611 variant is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g., transcription initiates in a promoter and proceeds through the DNA sequence coding for a monomeric eqFP611 variant. The promoter may be any DNA sequence which shows transcriptional activity in a suitable host cell of choice, (e.g., a bacterial cell, a mammalian cell, a yeast cell, or an insect cell) for expressing a monomeric eqFP611 variant of the invention. The promoter may be derived from genes encoding proteins either homologous or heterologous to the host cell.

Examples of suitable promoters for directing the transcription of the DNA sequence encoding the monomeric eqFP611 variant are the CMV promoter, Ubiquitin C promoter. SV40 promoter and MT-1 (metallothionein gene) promoter. An example of a suitable promoter for use in insect cells is the polyhedron promoter. Examples of suitable promoters for use in yeast host cells include promoters from yeast glycolytic genes or alcohol dehydrogenase genes or ADH2-4c promoters. Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gene, or the *Bacillus pumilus* xylosidase gene, or the phage Lambda PR or PL promoters or the *Escherichia coli* lac, trp or tac promoters.

The DNA sequence encoding a monomeric eqFP611 variant may also, if necessary, be operably connected to a suitable terminator, such as the human growth hormone terminator or the TPI1 or ADH3 terminators. The vector may further comprise elements such as polyadenylation signals (e.g., from SV40 or the adenovirus 5 E1b region), transcriptional enhancer sequences (e.g., the SV40 enhancer) and translational enhancer sequences (e.g., the ones encoding adenovirus VA RNAs).

The recombinant vector may further comprise a DNA sequence enabling the vector to replicate in the host cell in question. An example of such a sequence (when the host cell is a mammalian cell) is the SV40 origin of replication. When the host cell is a yeast cell, examples of suitable sequences enabling the vector to replicate are the yeast plasmid 2µ replication genes REP 1-3 and origin of replication. The vector may also comprise selectable markers, such as a gene that confers resistance to a drug, e.g., ampicillin, kanamycin, tetracyclin, chloramphenicol, puromycin, neomycin or hygromycin.

A further aspect relates a host cell having the DNA. Preferably, the host cell is transformed or transfected with a DNA construct comprising an expression vector. The DNA construct or the recombinant vector is suitably introduced into a host cell which may be any cell which is capable of expressing the present DNA construct and includes bacteria, yeast and higher eukaryotic, in particular mammalian, cells.

Examples of bacterial host cells which, on cultivation, are capable of expressing the DNA construct are Gram-positive bacteria, e.g., species of *Bacillus* or Gram-negative bacteria such as *E. coli*. The transformation of the bacteria may be effected by using competent cells in a known manner.

Examples of suitable mammalian cell lines are the HEK293 and the HeLa cell lines, primary cells, and the COS (e.g., ATCC CRL 1650), BHK (e.g., ATCC CRL 1632, ATCC CCL 10), CHL (e.g., ATCC CCL 39) or CHO (e.g., ATCC CCL 61) cell lines. Methods of transforming or transfecting mammalian cells and expressing DNA sequences introduced in the cells are known (21-23).

Examples of suitable yeast cells include cells of *Saccharomyces* spp. or *Schizosaccharomyces* spp., in particular strains of *Saccharomyces cerevisiae* or *Saccharomyces kluyveri*. Transformed cells may be selected by a phenotype determined by a selectable marker, commonly drug resistance or the ability to grow in the absence of a particular nutrient, e.g., leucine. A preferred vector for use in yeast is the POT1 vector. The DNA sequence encoding a monomeric eqFP611 variant may be preceded by a signal sequence and optionally a leader sequence, e.g., as described above. Further examples of suitable yeast cells are strains of *Kluyveromyces*, such as *K. lactis, Hansenula*, e.g., *H. polymorpha*, or *Pichia*, e.g., *P. pastoris* (24).

There is further provided a fluorescent reagent kit comprising at least one of: a) the DNA of SEQ ID No. 2, 4 or 6 b) an expression vector having the DNA of SEQ ID No. 2, 4 or 6 and c) a host cell having the DNA of SEQ ID No. 2, 4 or 6.

Further, there is provided a method for preparing a monomeric variant of the red fluorescent protein eqFP611, the method comprising:
  (a) cultivating a host cell so that the host cell produces a monomeric variant of the red fluorescent protein eqFP611; and
  (b) isolating and purifying said monomeric variant so produced by the host cell.

Suitably, the host cells, generally transformed or transfected as described above, are cultured in a suitable nutrient medium under conditions permitting the expression of a DNA encoding a monomeric eqFP611 variant. After completion of the culture, the cells may be recovered by centrifugal separation, and the recovered cells may be suspended in a water type buffer. Thereafter, the cells are typically disintegrated using an ultrasonic disintegrator or the like, so as to obtain a cell-free extract. A supernatant is obtained by centrifuging the cell-free extract, and then, a purified sample can be obtained from the supernatant by applying, singly or in combination. For instance, the following ordinary protein isolation and purification methods may be applied: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method and electrophoresis such as isoelectric focusing.

The medium used to culture the cells may be any conventional mediums suitable for growing the host cells, such as minimal or complex media containing appropriate supplements. Suitable media are available from commercial suppliers or may be prepared according to published protocols which are known.

We also provide a method for selecting cells expressing a protein of interest comprising:
 (a) introducing into cells a DNA encoding a protein of interest and a DNA encoding a monomeric variant of the red fluorescent protein eqFP611;
 (b) cultivating the cells from (a) under conditions permitting expression of the the monomeric variant and the protein of interest; and
 (c) selecting cultivated cells from (b) which express the monomeric variant.

We also encompass a method for measuring, in particular determining and/or monitoring, expression of a protein of interest in a cell comprising:
 (a) introducing into a cell a DNA encoding a monomeric variant of the red fluorescent protein eqFP611 fused to a DNA encoding a protein of interest the DNA being operably linked to and under the control of an expression control sequence which moderates expression of the protein of interest;
 (b) cultivating the cell under conditions suitable for the expression of the protein of interest; and
 (c) detecting the fluorescence emission of the monomeric variant as a means for measuring, in particular determining and/or monitoring, the expression of the protein of interest.

The term "operably linked" means that the regulatory sequences necessary for expression of the coding sequence are placed in the DNA molecule in the appropriate positions relative to the coding sequence so as to effect expression of the coding sequence. The same definition is sometimes applied to the arrangement of coding sequences and transcription control elements (EG promoters, enhances, and termination elements) in an expression vector. This definition is also sometimes applied to the arrangement of nucleic acid sequences of a first and a second nucleic acid molecule wherein a highbred nucleic acid molecule is generated.

With respect to the above-mentioned method, the monomeric eqFP611 variants act as a fluorescent labeling substances. This is to say, the monomeric eqFP611 variant is preferably purified as a fusion protein with a protein of interest, and the fusion protein is introduced into cells by methods such as the microinjection. By observing the distribution of the fusion protein over time, targeting activity of the protein of interest can be detected in the cells.

As already mentioned, the type of the protein of interest with which the monomeric eqFP611 variant is fused is not particularly limited. Preferred examples may include proteins localizing in cells, proteins specific for intracellular structures, in particular organelles, and targeting signals (e.g., a nuclear transport signal a mitochondrial presequence and the like). For example, by using a protein specific for an intracellular structure in particular intracellular organella, as a protein of interest, the distribution and movement of nucleus, mitochondria, an endoplasmic reticulum, a Golgi body, a secretory vesicle, a peroxisome or the like can be observed.

Accordingly, we provide a method for determining the localization, in particular intra- and/or extracellular localization, of a protein of interest comprising:
 (a) introducing into a cell a DNA encoding a monomeric variant of the red fluorescent protein eqFP611 fused to a DNA encoding a protein of interest the DNA being operably linked to and under the control of a suitable expression control sequence;
 (b) cultivating the cell under conditions suitable for the expression of the protein of interest; and
 (c) determining the localization of the protein of interest by detecting the fluorescence emission of the monomeric variant by optical means.

We further provide a method for localizing a subcellular structure in a cell comprising:
 (a) introducing into a cell a DNA encoding a monomeric variant of the red fluorescent protein eqFP611 fused to a DNA encoding a protein or peptide specific for a subcellular structure the DNA preferably being operably linked to and under the control of an expression control sequence which moderates expression of the protein or the peptide specific for a subcellular structure;
 (b) cultivating the cell under conditions suitable for the expression of the protein or the peptide specific for a subcellular structure; and
 (c) detecting the fluorescence emission of the monomeric variant as a means for localizing the subcellular structure in the cell.

Suitable proteins being specific for cellular substructures, in particular organelles are proteins being specific for endoplasmic reticulum, peroxisomes, nucleus, in particular organelles with pH values deviating from 7. Alternatively, the peptide specific for a subcellular structure may be a targeting signal, in particular cellulare substructures, for instance peroxisomes, endoplasmic reticulum, nucleus, mitochondria and the like. To this means, a monomeric eqFP611 variant may be fused to the targeting signal for labeling of cellular substructures, in particular for labeling the aforementioned organelles.

Further, we provide a method of comparing the effect of one or more test substance(s) on the expression and/or localization of a protein of interest comprising:
 (a) introducing into a cell a DNA encoding a monomeric variant of the red fluorescent protein eqFP611 fused to a DNA encoding a protein of interest the DNA being operably linked to and under the control of a suitable expression control sequence;
 (b) cultivating the cell under conditions suitable for the expression of the protein of interest in the presence and absence of the test substance(s);
 (c) determining the expression and/or localization of the protein of interest by detecting the fluorescence emission of the monomeric variant by optical means; and
 (d) comparing the fluorescence emission obtained in the presence and absence of the test substance(s) to determine the effect of the test substance(s) on the expression and/or localization of the protein of interest.

Finally, a method determines promoter activity in a cell comprising:
 (a) introducing into a cell a vector that is constructed such that DNA encoding a monomeric variant of the red fluorescent protein eqFP611 is located downstream of a promoter to be tested; and
 (b) detecting the fluorescence of the monomeric variant as a means for determining the activity of the promoter.

The fluorescence of the monomeric eqFP611 variant can be detected with a viable cell or with fixed cells. Such detection can be carried out using, for example, a fluorescence microscope (Axiophoto Filter Set 09 manufactured by Carl Zeiss) or an image analyzer (Digital Image Analyzer manufactured by ATTO). The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as microscope system. When an erecting microscope with a high-powered lens is used, a water immersion lens can be used. An appropriate filter set can be selected depending on the fluorescence wavelength of the monomeric eqFP611 variant. For example, since the wavelength of maximum absorption of the monomeric eqFP611 variant having the amino acid sequence as set forth in SEQ ID No. 1 is 558 nm, and the wavelength of maximum fluorescence thereof is 605 nm, circa 550 to 610 nm filter for fluorescence light can be used. Due to the large Stokes shift of the inventive monomeric eqFP611 variants, there is no cross-talk between the filters of a filter set when detecting the fluorescence of the monomeric eqFP611 variants.

Further, when viable cells are observed with time using a fluorescence microscope, photographing should be performed in a short time, and therefore a high sensitivity cooled CCD camera is used. In the cooled CCD camera, thermal noise is reduced by cooling CCD, and very weak fluorescent images can be clearly photographed with short-time exposure.

Alternatively or in combination to the above described fluorescence microscopy, the fluorescence may be detected by tracking, quantifying, and sorting of cells labeled with a monomeric eqFP611 variant using flow cytometry or fluorescence activated cell sorting (FACS).

To sum up, we provide novel monomeric variants of the red fluorescent protein eqFP611 exhibiting a large Stokes shift. This makes the monomeric variants in particular useful as labeling substances or markers (labels), preferably in biological and/or medicinal imaging. Preferably, the monomeric eqFP611 variants may be used as labeling substances for tracking cells, for instance in biological tissues or in cell cultures. The cells themselves may be living cells. Suitable cells may include differentiated cells and stem cells, particularly embryonic stem cells. Due to the superior stability of the monomeric eqFP611 variants upon fixation compounds, in particular paraformaldehyde, the monomeric variants of the tetrameric eqFP611 may also be used for labeling fixed cells. As already mentioned, the monomeric eqFP611 variants may further be used as labeling substances for selecting cells expressing a protein of interest. Furthermore, the monomeric eqFP611 variants may be used as labeling substances for measuring, in particular determining and/or monitoring, the expression, preferably the tissue specific expression, of a protein of interest. A further field of application of the monomeric eqFP611 variants relates to their use as labeling substances for determining and/or monitoring of cell differentiation, in particular stem cell differentiation, preferably embryonic stem cell differentiation. As already mentioned before, the monomeric eqFP611 variants may further be used as labeling substances for localization, in particular intra- and/or extracellular localization, of a protein of interest or for localization of a subcellular structure in a cell. Besides, the monomeric variants of eqFP611 may be used as markers for determining the promoter activity in a cell. A further area of application covers the use the inventive monomeric eqFP611 variants as labeling substances for measuring, in particular determining and/or monitoring, the gene expressions in cellular assays for screening of chemical compounds.

A preferred area of application relates to the use of the monomeric eqFP611 variants for diagnosing and/or monitoring of diseases. Preferably, the monomeric eqFP611 variants may be used in whole body imaging. For instance, the monomeric variants are used for monitoring of tumor development and/or for tracking of metastases. Furthermore, the monomeric eqFP611 variants may be used for determining and/or monitoring of peroxisomal biogenesis disorders.

The aforementioned fields of application impressively corroborate the versatility of the monomeric eqFP611 variants in the field of biology and medicine.

EXAMPLES

Example 1

Mutagenesis and Screening

The coding cDNA of tetrameric eqFP611 and its monomeric variants were ligated in the pQE-32 (Qiagen, Hilden, Germany). Monomerizing interface mutations were introduced by site-directed mutagenesis via overlap extension PCR (25). Random mutagenesis was performed according to the manufacturer's protocol using the Diversify PCR Random Mutagenesis Kit (Clontech Laboratories. Inc., Mountain View, Calif., USA), in conditions optimal for four to five mutations per 1000 bp. QuikChange Multi Site-Directed Mutagenesis Kit (Stratagene, La Jolla, Calif., USA) was used subsequently to spot mutations that act synergistically to promote folding. For this purpose, up to six oligonucleotide primers were applied in the mutagenesis reaction to a mixture of up to four different mutant templates. *E. coli* XL1-Blue or XL10-Gold® ultracompetent cells (Stratagene, La Jolla, Calif., USA) were transformed with the mutant plasmid libraries and bacterial colonies on agar plates were screened for fluorescence after overnight incubation at 37° C. using a UVA (365 nm) transilluminator (Benda, Wiesloch, Germany) and a fluorescence microscope (Axioplan I, Carl Zeiss Jena GmbH, Jena, Germany).

Example 2

Protein Expression, Purification and Gel Filtration Experiments

The eqFP611-variants carrying an N-terminal poly-His tag were expressed in *E. coli* M15 [pREP4](Qiagen, Hilden, Germany). The proteins were purified using Talon™ metal affinity resin (Clontech Laboratories. Inc., Mountain View, Calif., USA) and gel filtration (Superdex 200, Äkta System, GE Healthcare Biosciences, Little Chalfont, UK) as described (4, 26).

Example 3

Determination of Maturation Times

Maturation times at 37° C. were determined as described (4). The protein solutions were diluted to ensure an $OD_{\sim 560} \sim 0.1$ after maturation to avoid artificially shortened maturation times due to inner filter effects. Maturation time courses at 37° C. were recorded with a Cary Eclipse Spectrofluorometer (Varian Inc., Palo Alto, Calif., USA).

Example 4

Spectroscopic Characterization

Absorption spectra were recorded on a Cary 50 Spectrophotometer (Varian Inc., Palo Alto, Calif., USA). Fluorescence emission and excitation spectra were measures with a Cary Eclipse Spectrofluorometer (Varian Inc., Palo Alto, Calif., USA). The spectral characterization of the monomeric eqFP611 variants at pH extremes and photobleaching experiments were conducted as described in literature (12). Fluorescence lifetime measurements on the monomeric eqFP611 variants were performed with a Zeiss Axiovert 135 inverted microscope (Carl Zeiss Jena GmbH, Jena, Germany) by using a computer card for time-correlated single-photon counting (TIMEHARP 200, Pico-Quant, Berlin, Germany) similar to previous reports (4). The excitation light pulses (532 nm) were generated by mode-locked, frequency-doubled solid-state laser (GE-100, Time Bandwidth Products, Zürich, Switzerland). The fluorescence quantum yield in 1×PBS, pH 7.0, was determined using eqFP611 (quantum yield of 0.45) as a reference (4). Measurements of the molar extinction coefficient using the alkaline denaturation method (Ward, 2005) failed because of the extraordinary stability of the monomeric eqFP611 variants. High concentrations of 0.3-1.0 N NaOH had been applied to denature the monomeric eqFP611 variants and to calculate the chromophore concentration by using the extinction coefficient of denatured GFP (Green Fluorescent Protein) at pH 13 (27). After complete denaturation, not only was the acylimine bond of the red chromophore reduced, but a significant fraction of the resulting GFP-chromophore was also destroyed, resulting in artificially high molar extinction coefficients of up to 250,000 $M^{-1}$ $cm^{-1}$. Accordingly, the extinction coefficient of the monomeric eqFP611 variants were measured with the dynamic difference method.

Example 5

Vector Construction

For expression in mammalian cells, various monomeric eqFP611 variants were cloned into the pcDNA3 vector (Invitrogen, Carlsbad, Calif., USA). Human α-tubulin from the pEGFP-Tub vector (Clontech Laboratories, Inc., Mountain View, Calif., USA) was inserted into pcDNA3.1(−) downstream of the coding sequence of monomeric eqFP611 variants (Invitrogen, Carlsbad, Calif., USA). An endoplasmic reticulum retention signal (KDEL (SEQ ID No. 7)) (28) was introduced to the C-terminus of the monomeric eqFP611 variant and EGFP by PCR. The PCR products were inserted into the expression vector pCI-leader, encoding the signal peptide (METDT-LLLW-VLLL-WVP-GSTGD (SEQ ID No. 10)) from the murine Igκ chain.

Example 6

Eukaryotic Expression and Imaging

HeLa and HEK293 cells were grown on chambered cover glasses (Nalge Nunc International Corp., Rochester, N.Y., USA). Images were taken 24-48 h post-transfection using fluorescene microscopes (DM IRB, Leica Microsystems, Wetzlar, Germany, IX71, Olympus, Hamburg, Germany) equipped with a digital camera (C4742, Hamamatsu, Japan), a 100-W mercury lamp and standard FITC and TRITC filter sets. Subcellular localization of monomeric eqFP611 variants with peroxisomal targeting signals (PTS) were assayed by confocal microscopy. HEK293 cells were transfected with a pcDNA3 vector encoding monomeric eqFP611 variant with a peroxisomal targeting signal alone or in combination with a pcDNA3 vector encoding EGFP-H2B. Cells were fixed, permeabilized, and used directly for microscopic analysis or after immunostaining with an antiserum directed against human α-tubulin and an Alexa Fluor® 488-coupled secondary antibody. Cells were plated on circular quartz coverslips (Leica Microsystems, Wetzlar, Germany). Sandwiches of two coverslips were assembled with PBS/glycerol (13%/87% by volume) as a mounting medium. Images were collected on a Leica TCS 4Pi scanning confocal laser microscope (Leica Microsystems. Wetzlar. Germany) using a 100×, NA 1.35, glycerol immersion objective and 488-nm excitation for EGFP and Alexa Fluor® 488, whereas monomeric eqFP611 variant was excited at 561 nm. The emitted photos were registered by using two avalanche photodiodes (APDs; SPCM-AQR-14. Perkin-Elmer, Canada). A maximum-intensity projection of a 3D stack was prepared for presentation.

TABLE OF REFERENCES

1. Shaner, N. C. et al. J. Cell Sci. 120, 4247-4260 (2007).
2. Wiedenmann, J. Patent DE 197 18 640, 1-18 (1997).
3. Matz, M. V. et al. Nat. Biotechnol. 17, 969-973 (1999).
4. Wiedenmann, J. et al. Proc. Natl. Acad. Sci. USA 99, 11646-11651 (2002).
5. Yarbrough, J. et al. Proc. Natl. Acad. Sci. USA 98, 463-467 (2001).
6. Merzlyak, E. M. et al. Nat. Methods 4, 555-557 (2007).
7. Campbell, R. E. et al. Proc. Natl. Acad. Sci. USA 99, 7877-7882 (2002).
8. Shaner, N. C. et al. Nat. Biotechnol. 22, 1567-1572 (2004).
9. Karasawa, S., et al. Biochem. J. 381, 307-312 (2004).
10. Rizzo, M. A., et al. Nat. Biotechnol. 22, 445-449 (2004).
11. Sheherbo, D. et al. Nat. Methods 4, 741-746 (2007).
12. Wiedenmann, J. et al. J. Biomed. Opt. 10, 14003 (2005).
13. Schrader, M. & Fahimi, H. D., Histochem. Cell Biol. (Epub ahead of print) (2008).
14. Schrader, M. & Yoon, Y., Bioessays 29, 1105-1114 (2008).
15. Beaucage and Caruthers, Tetrahedron Letters 22, 1859-1869 (1981).
16. Matthes et al., EMBO Journal 3, 801-805 (1984).
17. Sambrook, J. et al., Molecular Cloning—A Laboratory Manual, Cold Spring Harbor Laboratory Press (1989).
18. Saiki et al., Science 239, 487-491 (1988).
19. Molecular Cloning: A Laboratory Manual, 2nd Ed., Cold Spring Harbor Laboratory, Cold Spring Harbor, N.Y., (1989)
20. Current Protocols in Molecular Biology, Supplement 1 to 38, John Wiley & Sons (1987-1997).
21. Kaufman and Sharp, J. Mol. Biol., 159, 601-621 (1982).
22. Southern and Berg, J. Mol. Appl. Genet., 1, 327-341 (1982).
23. Loyter et al., Proc. Natl. Acad. Sci USA, (1982).
24. Gleeson et al., J. Gen. Microbiol., 132, 3459-3465 (1986).
25. Ho S N, Hunt H D, Horton R M, Pullen J K, Pease L R (1989) Site-directed mutagenesis by overlap extension using the polymerase chain reaction. Gene 77: 51-59.
26. Wiedenmann J, Vallone B, Renzi F, Nienhaus K, Ivanchenko S, et al. (2005) Red fluorescent protein eqFP611 and its genetically engineered dimeric variants. Journal of Biomedical Optics 10: 14003.
27. Ward W W (2005) Biochemical and Physical Properties of Green Fluorescent Protein. In: Chalfie M, Kain S R, editors. Green fluorescent protein: properties, applications and protocols. 2nd ed. Hoboken, USA: Wiley and Sons. pp. 39-65.

28. Munro S, Pelham H R (1987) A C-terminal signal prevents secretion of luminal ER proteins. Cell 48: 899-907.

SUPPLEMENTAL TABLE 1

Peroxisomal localization of monomeric eqFP611 variants with different C-terminal sequences in HEK293 cells.

| C-terminal sequence | SEQ ID No. | Peroxisomal localization[a] 24 h post-transfection | 48 h post-transfection |
|---|---|---|---|
| $_{216}$HAVAKFCDLPSKLGRL$_{231}$[b] | 11 | ++++++ | ++++++ |
| $_{216}$HAVAKHSGLL$_{225}$ | 12 | +++++- | +++++- |
| $_{216}$HAVAKHSGL$_{224}$ | 13 | +++--- | +++--- |
| $_{216}$HAVAKFAGL$_{224}$ | 14 | ------ | ++---- |
| $_{216}$HAEAQFSGLL$_{225}$ | 15 | ------ | +----- |
| $_{216}$HAVAKHSG$_{223}$ | 16 | ------ | ------ |
| $_{216}$HAVAKHSGGG$_{225}$ | 17 | ------ | ------ |
| $_{216}$HAEAQFSG$_{223}$ | 18 | ------ | ------ |
| $_{216}$HAVAKFCDL$_{224}$ | 19 | ------ | ------ |
| $_{216}$HAVAKFAGGG$_{225}$ | 20 | ------ | ------ |
| $_{216}$HAVAKFAGLGGG$_{227}$[c] | 21 | ------ | ------ |

[a] Rating based on the co-localization with EGFP-SKL from complete (++++++) to absent (------)
[b] C-terminal sequence of wildtype eqFP611
[c] C-terminal sequence of monomeric eqFP variants as set forth in SEQ ID No. 1

Sequences (in accordance with the annexed sequence protocol)

SEQ ID No. 1 (denoted as mRuby):
MNSLIKENMRMKVVLEGSVNGHQFKCTGEGEGNPYMGTQTMRIKVIEGGP
LPFAFDILATSFMYGSRTFIKYPKGIPDFFKQSFPEGFTWERVTRYEDGG
VITVMQDTSLEDGCLVYHAQVRGVNFPSNGAVMQKKTKGWEPNTEMMYPA
DGGLRGYTHMALKVDGGGHLSCSFVTTYRSKKTVGNIKMPGIHAVDHRLE
RLEESDNEMFVVQREHAVAKFAGLGGG.

SEQ ID No. 2 (denoted as mRuby):
ATGAATTCACTGATCAAGGAAAATATGCGTATGAAGGTGGTCCTGGAAGG
TTCGGTCAACGGCCACCAATTCAAATGCACAGGTGAAGGAGAAGGCAATC
CGTACATGGGAACTCAAACCATGAGGATCAAAGTCATCGAGGGAGGACCC
CTGCCATTTGCCTTTGACATTCTTGCCACGAGCTTCATGTATGGCAGCCG
TACTTTTATCAAGTACCCGAAAGGCATTCCTGATTTCTTTAAACAGTCCT
TTCCTGAGGGTTTTACTTGGGAAAGAGTTACAAGATACGAAGATGGTGGA
GTCATTACCGTTATGCAGGACACCAGCCTTGAGGATGGCTGTCTCGTTTA
CCACGCCCAAGTCAGGGGGGTAAACTTTCCCTCCAATGGTGCCGTGATGC
AGAAGAAGACCAAGGGTTGGGAGCCTAATACAGAGATGATGTATCCAGCA
GATGGTGGTCTGAGGGGATACACTCATATGGCACTGAAAGTTGATGGTGG
TGGCCATCTGTCTTGCTCTTTCGTAACAACTTACAGGTCAAAAAAGACCG
TCGGGAACATCAAGATGCCCGGTATCCATGCCGTTGATCACCGCCTGGAA
AGGTTAGAGGAAAGTGACAATGAAATGTTCGTAGTACAACGCGAACACGC
AGTTGCCAAGTTCGCCGGGCTTGGTGGTGGTTAA

SUPPLEMENTAL TABLE 2

Fluorescence properties of monomeric eqFP variants as set forth in SEQ ID No. 1, its predecessors and other monomeric fluorescent proteins emitting in the orange to far-red spectral region.

| FP Variant | Excitation Maximum [nm] | Emission Maximum [nm] | Stokes shift | QY | $E_{mol}$ [$M^{-1} cm^{-1}$] | Relative Brightness[d] |
|---|---|---|---|---|---|---|
| mKO (Karasawa et al., 2004) | 548 | 559 | 11 | 0.6 | 51,600[c] | 1.0[c] |
| mOrange (Shaner et al., 2004) | 548 | 562 | 14 | 0.69 | 71,000[a] | 1.5[a] |
| tagRFP (Merzlyak et al., 2007) | 555 | 584 | 29 | 0.48 | 100,000[a] | 1.5[a] |
| mRuby | 558 | 605 | 47 | 0.35 | not applicable[a] 112,000[b] | 1.2[b] |
| eqFP611 (Wiedenmann et al., 2002) | 559 | 611 | 52 | 0.45 | 116,000[a] 146,000[b] | 1.6[a] 2.1[b] |
| RFP611 | 559 | 611 | 52 | 0.48 | 120,000[a] 151,000[b] | 1.8[a] 2.3[b] |
| mCherry (Shaner et al., 2004) | 587 | 615 | 28 | 0.22 | 72,000[a] | 0.5[a] |
| mRaspberry (Wang et al., 2004) | 598 | 625 | 27 | 0.15 | 86,000[a] | 0.4[a] |
| mKate (Sheherbo et al., 2007) | 588 | 635 | 47 | 0.33 | 45,000[a] | 0.5[a] |
| mPlum (Wang et al., 2004) | 590 | 649 | 59 | 0.1 | 41,000[a] 143,400[b,c] | 0.1[a] 0.4[b] |

[a] Concentration of the red chromophore determined by the alkaline denaturation method (Gross et al., 2000).
[b] Concentration of the red chromophore determined by the dynamic difference method.
[c] Concentration of the red chromophore deduced from the protein concentration as determined by the Bradford test.
[d] Product of QY and $E_{mol}$ compared to the brightness of EGFP (53,000 $M^{-1} cm^{-1}$ × 0.6) (Patterson et al., 1997).

-continued

SEQ ID No. 3 (denoted as mRuby, codon optimized variant):
MNSLIKENMRMKVVLEGSVNGHQFKCTGEGEGNPYMGTQTMRIKVIEGGP

LPFAFDILATSFMYGSRTFIKYPKGIPDFFKQSFPEGFTWERVTRYEDGG

VITVMQDTSLEDGCLVYHAQVRGVNFPSNGAVMQKKTKGWEPNTEMMYPA

DGGLRGYTHMALKVDGGGHLSCSFVTTYRSKKTVGNIKMPGIHAVDHRLE

RLEESDNEMFVVQREHAVAKFAGLGGG*

SEQ ID No. 4 (denoted as mRuby, codon optimized variant):
ATGAACAGCCTGATCAAAGAAAACATGCGGATGAAGGTGGTGCTGGAAGG

CAGCGTGAACGGCCACCAGTTCAAGTGCACCGGCGAGGGCGAGGGCAACC

CCTACATGGGCACCCAGACCATGCGGATCAAAGTGATCGAGGGCGGACCT

CTGCCCTTCGCCTTCGACATCCTGGCCACATCCTTCATGTACGGCAGCCG

GACCTTCATCAAGTACCCCAAGGGCATCCCCGATTTCTTCAAGCAGAGCT

TCCCCGAGGGCTTCACCTGGGAGAGAGTGACCAGATACGAGGACGGCGGC

GTGATCACCGTGATGCAGGACACCAGCCTGGAAGATGGCTGCCTGGTGTA

CCATGCCCAGGTCAGGGGCGTGAATTTTCCCAGCAACGGCGCCGTGATGC

AGAAGAAAACCAAGGGCTGGGAGCCCAACACCGAGATGATGTACCCCGCT

GACGGCGGACTGAGAGGCTACACCCACATGGCCCTGAAGGTGGACGGCGG

AGGGCACCTGAGCTGCAGCTTCGTGACCACCTACCGGTCCAAGAAAACCG

TGGGCAACATCAAGATGCCCGGCATCCACGCCGTGGACCACCGGCTGGAA

AGGCTGGAAGAGTCCGACAACGAGATGTTCGTGGTGCAGCGGGAGCACGC

CGTGGCCAAGTTCGCCGGCCTGGGCGGAGGGTGA

SEQ ID No. 5 (denoted as mRuby, with peroxisomal targeting signal):
MNSLIKENMRMKVVLEGSVNGHQFKCTGEGEGNPYMGTQTMRIKVIEGGP

LPFAFDILATSFMYGSRTFIKYPKGIPDFFKQSFPEGFTWERVTRYEDGG

VITVMQDTSLEDGCLVYHAQVRGVNFPSNGAVMQKKTKGWEPNTEMMYPA

DGGLRGYTHMALKVDGGGHLSCSFVTTYRSKKTVGNIKMPGIHAVDHRLE

RLEESDNEMFVVQREHAVAKFCDLPSKLGRL

SEQ ID No. 6 (denoted as mRuby, with peroxisomal targeting signal):
ATGAATTCACTGATCAAGGAAAATATGCGTATGAAGGTGGTCCTGGAAGG

TTCGGTCAACGGCCACCAATTCAAATGCACAGGTGAAGGAGAAGGCAATC

CGTACATGGGAACTCAAACCATGAGGATCAAAGTCATCGAGGGAGGACCC

CTGCCATTTGCCTTTGACATTCTTGCCACGAGCTTCATGTATGGCAGCCG

TACTTTTATCAAGTACCCGAAAGGCATTCCTGATTTCTTTAAACAGTCCT

TTCCTGAGGGTTTTACTTGGGAAAGAGTTACAAGATACGAAGATGGTGGA

GTCATTACCGTTATGCAGGACACCAGCCTTGAGGATGGCTGTCTCGTTTA

CCACGCCCAAGTCAGGGGGGTAAACTTTCCCTCCAATGGTGCCGTGATGC

AGAAGAAGACCAAGGGTTGGGAGCCTAATACAGAGATGATGTATCCAGCA

GATGGTGGTCTGAGGGGATACACTCATATGGCACTGAAAGTTGATGGTGG

TGGCCATCTGTCTTGCTCTTTCGTAACAACTTACAGGTCAAAAAAGACCG

TCGGGAACATCAAGATGCCCGGTATCCATGCCGTTGATCACCGCCTGGAA

AGGTTAGAGGAAAGTGACAATGAAATGTTCGTAGTACAACGCGAACACGC

AGTTGCCAAGTTCTGTGACCTTCCATCCAAACTGGGACGTCTTTGA

---

The invention claimed is:

1. A DNA encoding a monomeric variant of red fluorescent protein eqFP611, wherein the monomeric variant comprises an amino acid sequence selected from the group consisting of SEQ ID NO: 1 and SEQ ID NO: 5.

2. A DNA comprising a nucleotide sequence selected from the group consisting of SEQ ID NO: 2, SEQ ID NO: 4, and SEQ ID NO: 6.

3. An expression vector comprising expression control sequences and the DNA according to claim 1, wherein the expression control sequences are operably linked to the DNA.

4. An expression vector comprising expression control sequences and the DNA according to claim 2, wherein the expression control sequences are operably linked to the DNA.

5. An isolated host cell transformed or transfected with the DNA according to claim 1.

6. An isolated host cell transformed or transfected with the DNA according to claim 2.

7. An isolated host cell transformed or transfected with the expression vector according to claim 3.

8. The isolated host cell according to claim 5, selected from the group consisting of a mammalian cell, a bacterial cell, a yeast cell, and an insect cell.

9. The isolated host cell according to claim 7, selected from the group consisting of a mammalian cell, a bacterial cell, a yeast cell, and an insect cell.

10. A fluorescent reagent kit comprising at least one of:
   a) a DNA comprising the nucleotide sequence of SEQ ID NO: 2, 4, or 6,
   b) an expression vector comprising a DNA comprising the nucleotide sequence of SEQ ID NO: 2, 4, or 6, and
   c) an isolated host cell transformed or transfected with a DNA comprising the nucleotide sequence of SEQ ID NO: 2, 4, or 6.

11. A method of preparing a monomeric variant of red fluorescent protein eqFP611 comprising:
   (a) cultivating the isolated host cell according to claim 5 so that the host cell produces a monomeric variant of the red fluorescent protein eqFP611, wherein the monomeric variant comprises the amino acid sequence of SEQ ID NO: 1 or SEQ ID NO: 5; and
   (b) isolating and purifying said monomeric variant so produced by the host cell.

12. A method of preparing a monomeric variant of red fluorescent protein eqFP611 comprising:
   (a) cultivating the isolated host cell according to claim 7 so that the host cell produces a monomeric variant of the red fluorescent protein eqFP611, wherein the monomeric variant comprises the amino acid sequence of SEQ ID NO: 1 or SEQ ID NO: 5; and
   (b) isolating and purifying said monomeric variant so produced by the host cell.

13. A method of preparing a monomeric variant of red fluorescent protein eqFP611 comprising:
   (a) cultivating the isolated host cell according to claim 8 so that the host cell produces a monomeric variant of the red fluorescent protein eqFP611, wherein the monomeric variant comprises the amino acid sequence of SEQ ID NO: 1 or SEQ ID NO: 5; and
   (b) isolating and purifying said monomeric variant so produced by the host cell.

* * * * *